United States Patent [19]
Reed et al.

[11] Patent Number: 5,372,812
[45] Date of Patent: Dec. 13, 1994

[54] COMPOSITION AND METHOD FOR ACCELERATION OF CLOT LYSIS

[75] Inventors: Guy L. Reed, Cambridge, Mass.; Gary R. Matsueda, Princeton, N.J.; Edgar Haber, New York, N.Y.

[73] Assignee: The General Hospital Corporation, Boston, Mass.

[21] Appl. No.: 943,372

[22] Filed: Sep. 10, 1992

Related U.S. Application Data

[63] Continuation of Ser. No. 589,003, Sep. 27, 1990, abandoned, which is a continuation-in-part of Ser. No. 177,222, Apr. 4, 1988, abandoned.

[51] Int. Cl.$^5$ .................. A61K 37/54; A61K 37/547; A61K 39/00; C07K 15/28
[52] U.S. Cl. .................. 424/145.1; 424/94.64; 424/85.8; 424/94.63; 530/388.25; 530/388.26
[58] Field of Search .................. 424/94.63, 94.64, 85.8; 530/388.26, 388.25

[56] References Cited

U.S. PATENT DOCUMENTS

| | | | |
|---|---|---|---|
| 4,147,765 | 4/1979 | Stephan et al. | 424/12 |
| 4,198,335 | 4/1980 | Collen | 530/387 |
| 4,216,291 | 8/1980 | Collen | 435/7 |
| 4,245,040 | 1/1981 | Pilgeram | 435/13 |
| 4,273,873 | 6/1981 | Sugitachi et al. | 435/180 |
| 4,346,029 | 8/1982 | Collen | 530/387 |
| 4,368,149 | 1/1983 | Masuho et al. | 260/112 |
| 4,414,148 | 11/1983 | Jansen et al. | 260/112 |
| 4,455,290 | 6/1984 | Olexa et al. | 424/1.1 |
| 4,470,925 | 9/1984 | Auditore-Hargreaves | 260/112 |
| 4,474,893 | 10/1984 | Reading | 436/547 |
| 4,545,988 | 10/1985 | Nakayama et al. | 424/94 |
| 4,671,958 | 6/1987 | Rodwell et al. | 424/85 |
| 4,673,573 | 6/1987 | Ferres et al. | 424/94.63 |
| 4,722,903 | 2/1988 | Kudryk et al. | 435/7 |
| 4,758,524 | 7/1988 | Bundesen et al. | 436/548 |
| 4,833,085 | 5/1989 | Schaumann et al. | 435/240.27 |
| 4,916,070 | 4/1990 | Matsueda et al. | 435/172.2 |
| 4,927,916 | 5/1990 | Matsueda et al. | 530/387 |
| 5,116,613 | 5/1992 | Haber et al. | 424/85.8 |

FOREIGN PATENT DOCUMENTS

| | | |
|---|---|---|
| 25387/84 | 9/1984 | Australia . |
| 34872/84 | 3/1985 | Australia . |
| 32845/89 | 11/1989 | Australia . |
| 0063002 | 10/1982 | European Pat. Off. . |
| 0088994 | 9/1983 | European Pat. Off. . |
| 0120694 | 10/1984 | European Pat. Off. . |
| 0125023 | 11/1984 | European Pat. Off. . |
| 0142905 | 5/1985 | European Pat. Off. . |
| 0146050 | 6/1985 | European Pat. Off. . |
| 159025 | 10/1985 | European Pat. Off. . |
| 0187658 | 7/1986 | European Pat. Off. . |

(List continued on next page.)

OTHER PUBLICATIONS

Collen and Verstraete, "$\alpha_2$–Antiplasmin consumption and fibrinogen breakdown during thrombolytic therapy", *Thrombosis Research* 14:631–639 (1979).

(List continued on next page.)

*Primary Examiner*—Jacqueline Stone
*Attorney, Agent, or Firm*—Sterne, Kessler, Goldstein & Fox

[57] ABSTRACT

The present invention relates to a novel treatment for blood clots within a patient or myocardial infarction which comprises administering a hapten-binding molecule capable of preventing inhibition of plasmin by endogenous alpha-2-antiplasmin. The invention also relates to a treatment for blood clots within a patient or myocardial infarction comprising coadministrating the hapten-binding molecule of the invention together with a thrombolytic agent capable of either dissolving fibrin-platelet clots or inhibiting their formation. The therapy of the invention is capable of increasing clot lysis while minimizing fibrinogen breakdown and preventing the reocclusion of the affected coronary artery. The therapy of the present invention is capable of achieving this goal even in the absence of heparin and when the concentration of thrombolytic agent is lower than that required by other potential therapies.

11 Claims, 21 Drawing Sheets

FOREIGN PATENT DOCUMENTS

| | | |
|---|---|---|
| 0271227 | 6/1988 | European Pat. Off. . |
| 61-268630 | 11/1986 | Japan ............................ A61K 39/395 |
| 2122219 | 1/1984 | United Kingdom . |
| WO83/03678 | 10/1983 | WIPO . |
| WO83/03679 | 10/1983 | WIPO . |
| WO83/03971 | 11/1983 | WIPO . |
| WO85/00974 | 3/1985 | WIPO . |
| WO86/01533 | 3/1986 | WIPO . |
| WO87/05934 | 10/1987 | WIPO . |
| WO87/06263 | 10/1987 | WIPO . |
| WO87/06836 | 11/1987 | WIPO . |
| WO88/03559 | 5/1988 | WIPO . |
| WO89/09817 | 10/1989 | WIPO . |

OTHER PUBLICATIONS

Collen and Wiman, "Turnover of antiplasmin, the fast-acting plasmin inhibitor of plasma", *Blood* 53(2):313–324 (Feb. 1979).

Kane, "Fibrinolysis—A Review", *Annals of Clinical and Laboratory Science* 14(6):443–449 (1984).

Mudgett-Hunter et al., "Binding and structural diversity among high-affinity monoclonal anti-digoxin antibodies", *Molecular Immunology* 22(4):477–488 (1985).

Ouchi and Warren, "Detection of intravascular thrombi by means of $I^{131}$-labeled plasmin", *Surgery* 51(1):42–49 (Jan. 1962).

Agnelli et al., "The comparative effects of recombinant hirudin (CGP 39393) and standard heparin on thrombus growth in rabbits", *Thrombosis and Haemostasis* 63(2):204–207 (1990).

Agnelli et al., "A comparison of the thrombolytic and hemorrhagic effects of tissue-type plasminogen activator and streptokinase in rabbits", *Circulation* 72(1):178–182 (1985).

Agnelli et al., "Sustained thrombolysis with DNA", *Blood* 66(2):399–401 (Aug. 1985).

Angles-Cano, E. R., "Tissue plasminogen activator determination with a fibrin-supported film", *Chem. Abstracts* 104:307–308, Abstract No. 144639d (1986).

Aoki, N. et al., "Fibrin-associated plasminogen activation in $\alpha_2$-plasmin inhibitor deficiency", *Blood* 62(5):1118–1122 (Nov. 1983).

Bode et al., "Conjugation to antifibrin Fab' enhances fibrinolytic potency of single-chain urokinase plasminogen activator", *Circulation* 81(6):1974–1980 (Jun. 1990).

Bode et al., "Antibody-directed urokinase: a specific fibrinolytic agent", *Science* 229:765–767 (Aug. 23, 1985).

Bode et al., "Thrombolysis by a fibrin-specific antibody Fab'urokinase conjugate", *J. Mol. Cell Cardiol.* 19:335–341 (1987).

Bode et al., "Antibody-directed fibrinolysis", *J. Biol. Chem.* 264(2):944–948 (Jan. 15, 1989).

Boulianne et al., "Production of functional chimaeric mouse/human antibody", *Nature* 312:643–646 (Dec. 13, 1984).

Branscomb et al., "Bispecific monoclonal antibodies produced by somatic cell fusion increase the potency of tissue plasminogen activator", *Thrombosis and Haemostasis* 64(2):260–266 (1990).

Brennan et al., "Preparation of bispecific antibodies by chemical recombination of monoclonal immunoglobulin $G_1$ fragments", *Science* 229:81–83 (Jul. 5, 1985).

Carrasquillo et al., "Radioimmunodetection of human melanoma with monoclonal antibodies and Fab fragments", *Radioimaging and Radioimmunotherapy*, Burchiol and Rhodes, Eds., Elsevier Science Publishing Co., Inc., pp. 357–368 (1983).

Charpie et al., "A bispecific antibody enhances the fibrinolytic potency of single-chain urokinase", *Biochemistry* 29(27):6374–6378 (1990).

Collen et al., "Thrombolysis with human extrinsic (tissue-type) plasminogen activator in rabbits with experimental jugular vein thrombosis", *J. Clin. Invest.* 71:368–376 (Feb. 1983).

Collen et al., "Thrombolytic and pharmacokinetic properties of chimeric tissue-type ad urokinase-type plasminogen activators", *Circulation* 84(3):1216–1234 (Sep. 1991).

Collen et al., "Synergism of thrombolytic agents in vivo", *Circulation* 74(4):838–842 (Oct. 1986).

DeWood et al., "Prevalence of total coronary occlusion during the early hours of transmural myocardial infarction", *New England J. of Medicine* 303(16):897–902 (Oct. 16, 1980).

Dorai et al., "The effect of dihydrofolate reductase-mediated gene amplification on the expression of transfected immunoglobulin genes", *J. Immunol.* 139(12):4232–4241 (Dec. 15, 1987).

(List continued on next page.)

OTHER PUBLICATIONS

Duberstein, R., "Scientists develop new technique for producing bispecific monoclonals", *Genetic Engineering News* 6:22 (1986).

Emeis, J. J. and Verheijen, J. H., "Thrombolytic properties in a rabbit jugular vein thrombosis model of a tissue-type plasminogen activator mutant lacking the growth factor- and kringle one-domains", *Arzneim.-Forsch./Drug Res.* 42(3):358–362 (1992).

Fisher et al., "Isolation and characterizaton of the human tissue-type plasminogen activator structural gene including its 5' flanking region", *J. Biol. Chem.* 260(20):11223–11230 (Sep. 15, 1985).

Gardell et al., "Effective thrombolysis without marked plasminemia after bolus intravenous administration of vampire bat salivary plasminogen activator in rabbits", *Circulation* 84(1):244–253 (Jul. 1991).

Haber, E. et al., "Antibody targeting as a thrombolytic strategy", *Annals of the New York Academy of Sciences*, pp. 365–381 (Dec. 1992).

Hessel et al., "Primary structure of human fibrinogen and fibrin", *Eur. J. Biochem.* 98:521–534 (1979).

Kudryk et al., "Specificity of a monoclonal antibody for the $NH_2$-terminal region of fibrin", *Molec. Immunol.* 21(1):89–94 (1984).

Laffel, G. L. and Braunwald, E., "A new strategy for the treatment of acute myocardial infarction (first of two parts)", *New England J. of Medicine* 311(11):710–717 (Sep. 13, 1984).

Hauranieh et al., "Monoclonal antibodies to human cross-linked fibrin", *Fed. Proc.* 44:1846, Abstract No. 8381 (1985).

Hui et al., "Immunodection of human fibrin using monoclonal antibody-64C5 in an extracorporeal chicken model", *Thrombosis and Haemostasis* 54(2):524–527 (1985).

Hui et al., "Monoclonal antibodies of predetermined specificity for fibrin: a rational approach to monoclonal antibody production", *Hybridoma* 5(3):215–222 (1986).

Hui et al., "Monoclonal antibodies to a synthetic fibrin-like peptide bind to human fibrin but not fibrinogen", *Science* 222:1129–1132 (Dec. 9, 1983).

Ito, R. K., "Fibrinolysis studies: fibrinogen-specific antibody as carriers for fibrinolytic agents", *Fed. Proc.* 44:1846, Abstract No. 8382 (1985).

Kabnick, K. S. and Housman, D. E., "Determinants that contribute to cytoplasmic stability of human c-fos and $\beta$-globin mRNAs are located at several sites in each mRNA", *Mol. Cell. Biol.* 8(8):3244–3250 (Aug. 1988).

Kato et al., "A specific immunoassay system for hybrid type antigens", *Chem. Abstracts* 94:325, Abstract No. 61048j (1981).

Kimura, S. et al., "Acceleration of fibrinolysis by the N-terminal peptide of $\alpha_2$-plasmin inhibitor", *Blood* 66(1):157–160 (Jul. 1985).

Kudryk et al., "A monoclonal antibody with ability to distinguish between $NH_2$-terminal fragments derived from fibrinogen and fibrin", *Molecular Immunology* 20(11):1191–1200 (1983).

Laffel, G. L. and Braunwald, E., "A new strategy for the treatment of acute myocardial infarction (second of two parts)", *New England J. of Medicine* 311(12):770–776 (Sep. 20, 1984).

Lanzavecchia, A. Scheidegger, D., "The use of hybrid hybridomas to target human cytotoxic T lymphocytes", *Eur. J. Immunol.* 17:105–111 (1987).

Larsen et al., "Protein Engineering of novel plasminogen activators with increased thrombolytic potency in rabbits relative to activase", *J. of Biol. Chem.* 266(13):8156–8161 (May 5, 1991).

Lawn et al., "The nucleotide sequence of the human $\beta$-globin gene", *Cell* 21:647–651 (Oct. 1980).

Lijnen et al., "Comparative fibrinolytic properties of staphylokinase and streptokinase in animal models of venous thrombosis", *Thrombosis and Haemostasis* 66(4):468–473 (1991).

Lijnen et al., "Biochemical and thrombolytic properties of a low molecular weight form (comprising $Leu^{144}$ through $Leu^{411}$) of recombinant single-chain urokinase-type plasminogen activator", *J. of Biol. Chem.* 263(12):5594–5598 (Apr. 25, 1988).

Liu et al., "Heteroantibody duplexes target cells for lysis by cytotoxic T lymphocytes", *Proc. Natl. Acad. Sci. USA* 82:8648–8652 (Dec. 1985).

Love et al., "Recombinant antibodies possessing novel effector functions", *Meth. Enzymol.* 178:515–527 (1989).

Lukacova et al., "Inhibition of factor XIII activation by (List continued on next page.)

OTHER PUBLICATIONS an anti-peptide monoclonal antibody", *Biochemistry* 30(42):10164–10170 (1991).

Martin et al., "Properties of a novel plasminogen activator (BM 06.022) produced in *Escherichia coli*", *Z. Kardiol.* 79(Suppl. 3):167–170 (1990).

Matsueda et al., "A monoclonal antibody specific for the C terminus of fibrinogen and fibrin gamma chains", *FASEB J.* 2:A1411, Abstract No. 6480 (1988).

Matsueda et al., "Fibrin-specific monoclonal antibodies are elicited by immunization with a synthetic fibrin-like peptide", *Proceedings: Fibrinogen structural variants and interactions,* vol. 3, Henschen et al., Eds. Walterde Gruyter Berline, New York, pp. 43–50 (1985).

Matsueda et al., "Monoclonal antibodies specific for human fibrin monomer", *Fed. Proc.* 42(7):1992, Abstract No. 1375 (May 1, 1983).

Matsueda et al., "Detection of thrombi: a chicken model using monoclonal antibody which binds to human fibrin but not fibrinogen", *Haemostasis* 14(1):44, Abstract No. 75 (1984).

Matsueda et al., "Synthetic fibrin-like peptides used as antigens yield fibrin-specific antibodies", *Peptides Structure and Function, Proceedings of the 8th American Peptide Symposium,* Hruby and Rich, Eds., pp. 873–876 (1983).

Matsuo et al., "Thrombolytic effect of single-chain prourokinase in a rabbit jugular vein thrombosis model", *Thrombosis Research* 42:187–194 (1986).

Milstein et al., "Hybrid hybridomas and their use in immunohistochemistry", *Nature* 305:537–540 (Oct. 6, 1983).

McCabe et al., "A diagnostic-prognostic test for bladder cancer using a monoclonal antibody-based enzyme-linked immunoassay for detection of urinary fibrin(ogen) degradation products", *Cancer Res.* 44:5886–5893 (Dec. 1984).

Morrison, S. L. and Oi, V. T., "Genetically engineered antibody molecules", *Adv. Immunol.* 44:65–92 (1989).

Morrison et al., "Transfectomas provide novel chimeric antibodies", *Science* 229:1202–1207 (Sep. 20, 1985).

Morrison et al., "Chimeric human antibody molecules: mouse antigen-binding domains with human constant region domains", *Proc. Natl. Acad. Sci. USA* 81:6851–6855 (Nov. 1984).

Munro, A., "Uses of chimaeric antibodies", *Nature* 312:597 (Dec. 13, 1984).

Neuberger et al., "Recombinant antibodies possessing novel effector functions", *Nature* 312:604–608 (Dec. 13, 1984).

Neuberger et al., "A hapten-specific chimaeric IgE antibody with human physiological effector function", *Nature* 314:268–270 (Mar. 21, 1985).

Nisonoff, A. and Mandy, W. J., "Quantitative estimation of the hybridization of rabbit antibodies", *Nature* 194:355–359 (Apr. 28, 1962).

Nossel, H. L., "Relative proteolysis of the fibrinogen B$\beta$ Chain by thrombin and plasmin as a determinant of thrombosis", *Nature* 291:165–167 (May 14, 1981).

Oi et al., "Chimeric antibodies", *BioTechniques* 4(3):214–221 (1986).

Pacella et al., "Induction of fibrin-specific antibodies by immunization with synthetic peptides that correspond to amino termini of thrombin cleavage sites", *Molecular Immunology* 20(5):521–527 (1983).

Philpott et al., "Selective cytotoxicity of hapten-substituted cells with an antibody-enzyme conjugate", *J. Immunol.* 111(3):921–929 (Sep. 1973).

Philpott et al., "Selective binding and ctotoxicity of rat basophilic leukemia cells (RBL-1) with immunoglobulin E-biotin and avidin-glucose oxidase conjugates", *J. Immunol.* 125(3):1201–1209 (Sep. 1980).

Pizzo, S. V. et al., "The effect of plasmin on the subunit structure of human fibrin", *J. Biol. Chem.* 248(13):4574 –4583 (Jul. 10, 1973).

Reed et al., "Inhibition of clot-bound $\alpha$2-antiplasmin enhances in vivo thrombolysis", *Circulation* 82(1):164–168 (Jul. 1990).

Rajagopalan et al., "A nonantigenic covalen streptokinase-polyethylene glycol complex with plasminogen activator function", *J. Clin. Invest* 75:413–419 (Feb. 1985).

Whitaker et al., "Measurement of crosslinked fibrin degradation products using monoclonal antibodies: use in the study of intravascular coagulation", *Pathology* 16(3):357–358 (Jul. 1984).

Rosebrough et al., "Radioimmunoimaging of venous (List continued on next page.)

OTHER PUBLICATIONS thrombi using iodine-131 monoclonal antibody", *Radiology* 156:515-517 (1985).

Runge et al., "Antibody-enhanced thrombolysis: capture of tissue plasminogen activator by a bispecific antibody and direct targeting by an antifibrin-tissue plasminogen activator conjugate in vivo", *Trans. Assoc. Am. Phys.* 100:250-255 (1987).

Runge et al., "Conjugation to an antifibrin monoclonal antibody enhances the fibrinolytic potency of tissue plasminogen activator in vitro", *Biochemistry* 27:1153-1157 (1988).

Runge et al., "Increasing selectivity of plasminogen activators with antibodies", *Clin. Res.* 36:501-506 (1988).

Runge et al., "Antibody-enhanced thrombolysis: targeting of tissue plasminogen activator in vivo", *Proc. Natl. Acad. Sci. USA* 84:7659-7662 (Nov. 1987).

Runge et al., "Antibody-directed fibrinolysis: a bispecific (Fab')$_2$ that binds to fibrin and tissue plasminogen activator", *Bioconjugate Chemistry* 1(4):274-277 (1990).

Sakata, Y. and Aoki, N., "Significance of cross-linking of $\alpha_2$-plasmin inhibitor to fibrin in inhibition of fibrinolysis and in hemostasis", *J. Clin. Invest.* 69:536-542 (Mar. 1982).

Scheefers-Borchel et al., "Discrimination between fibrin and fibrinogen by a monoclonal antibody against a synthetic peptide", *Proc. Natl. Acad. Sci. USA* 82:7091-7095 (Oct. 1985).

Schnee et al., "Construction and expression of a recombinant antibody-targeted plasminogen activator", *Proc. Natl. Acad. Sci. USA* 84:6904-6908 (Oct. 1987).

Sevilla et al., "Plasminogen activator-anti-human fibrinogen conjugate", *Fed. Proceedings* 44(4):1073, Abstract No. 3872 (Mar. 5, 1985).

Sevilla et al., "Plasminogen activator-anti-human fibrinogen conjugate", *Biochem. Biophys. Res. Commun.* 130(1):91-96 (Jul. 16, 1985).

Sharma et al., "Medical intelligence—thrombolytic therapy", *New England J. of Medicine* 306(21):1268-1276 (May 27, 1982).

Sharon et al., "Expression of a $V_HC_K$ chimaeric protein in mouse myeloma cells", *Nature* 309:364-367 (May 24, 1984).

Sobel et al., "Characterization of a crosslink-containing fragment derived from the $\alpha$ polymer of human fibrin and its application in immunologic studies using monoclonal antibodies", *Thromb. Haemostasis* 46(1):240, No. 0758 (1981).

Sobel et al., "Augmented and sustained plasma concentrations after intramuscular injections of molecular variants and deglycosylated forms of tissue-type plasminogen activators", *Circulation* 81(4):1362-1373 (Apr. 1990).

Soria et al., "Monoclonal antibodies that react preferentially with fibrinogen degradation products or with cross-linked fibrin split products", *Ann. N.Y. Acad. Sci.* 408:665-666 (1983).

Staerz et al., "Hybrid hybridoma producing a bispecific monoclonal antibody that can focus effector T-cell activity", *Proc. Natl. Acad. Sci. USA* 83:1453-1457 (Mar. 1986).

Stump et al., "Comparative thrombolytic properties of single-chain forms of urokinase-type plasminogen activator", *Blood* 69(2):592-596 (Feb. 1987).

Thorpe et al., "Single shot intrasplenic immunization: an advantageous procedure for production of monoclonal antibodies specific for human fibrin fragments", *Hybridoma* 3(4):381-384 (1984).

Tucker et al., "Sequence of the cloned gene for the constant region of murine $\gamma$2b immunoglobulin heavy chain", *Science* 206:1303-1306 (Dec. 14, 1979).

van Zonneveld et al., "Structure and function of human tissue-type plasminogen activator (t-PA)", *J. Cell. Biochem.* 32:169-178 (1986).

Verde et al., "Identification and primary sequence of an unspliced human urokinase poly(A)+ RNA", *Proc. Natl. Acad. Sci. USA* 81:4727-4731 (Aug. 1984).

Waldman, T. A., "Monoclonal antibodies in diagnosis and therapy", *Science* 252:1657-1662 (Jun. 21, 1991).

Williams et al., "Production of antibody-tagged enzymes by myeloma cells: application to DNA polymerase I Klenow fragment", *Gene* 43:319-324 (1986).

International Search Report for WO87/06240 (PCT/US87/00860).

International Search Report for WO88/03559 (PCT/US87/02968).

European Search Report for EP271,227 (EP 87310006).

European Search Report for EP 89 30 3293.

Reed, G. L. et al., *Proc. Natl. Acad. Sci. USA* 87:1114 (1990).

Reed, G. L. et al., *J. Am. Coll. Cardiol.* 13:2A (1989).

Reed, G. L. et al., *Trans. Assoc. Am. Phys.* 101:250 (1988).

Kumada, T. et al., *Thromb. Res.* 36:153 (1984).

Mimuro, J. et al., *Blood* 69:446 (1987).

Hattey, E. et al., *Thromb. Res.* 45:485 (1987).

Gold, H. K. et al., *Circulation* 73:347 (1986).

Matsuo, O. et al., *Thromb. Haemost.* 45:225 (1981).

Plow, E. F. et al., *J. Biol. Chem.* 255:2902 (1980).

Wiman, B. et al., *Scan. J. Clin. Lab. Invest.* 43:27 (1983).

Miles, L. A. et al., *Blood* 59:1246 (1982).

Zamarron, C. et al., *Thromb. Res.* 35:335 (1984).

COMPOSITION AND METHOD FOR ACCELERATION OF CLOT LYSIS

This application is a continuation of application Ser. No. 07/589,003, filed Sep. 27, 1990 now abandoned which application is a continuation-in-part of U.S. application Ser. No. 07/177,222 filed Apr. 4, 1988, now abandoned, which disclosure is herein incorporated in its entirety.

FIELD OF THE INVENTION

The present invention relates to a treatment for myocardial infarction and blood clots within a patient, and more specifically to a therapy which enhances clot lysis comprising administering an antibody directed to alpha-2-antiplasmin. The invention also relates to a treatment for enhancing clot lysis comprising administering an antibody directed toward alpha-2-antiplasmin together with a thrombolytic agent.

BACKGROUND OF THE INVENTION

The initiating event of many myocardial infarctions (heart attacks) is the hemorrhage into atherosclerotic plaque. Such hemorrhage often results in the formation of a thrombus (or blood clot) in the coronary artery which supplies the infarct zone (i.e., an area of coagulation necrosis which results from an obstruction of blood circulation). This thrombus is composed of a combination of fibrin and blood platelets. The formation of a fibrin-platelet clot has serious clinical ramifications. The degree and duration of the occlusion caused by the fibrin-platelet clot determines the mass of the infarct zone and the extent of damage.

A. Treatment for Myocardial Infarction

The primary goal of current treatment for myocardial infarction involves the rapid dissolution of the occluding thrombus and the restoration of blood flow ("reperfusion"). In order to be effective, a successful therapy must be capable of discriminating between a fibrin-platelet clot and the fibrin precursor, fibrinogen. The use of an agent which fails to exhibit such specificity may increase the risk of general hemorrhage to the patient. A successful therapy must be capable of sustained effect so that reformation of the clot does not occur after the cessation of therapy. If the fibrin-platelet clot is able to reform, then the affected artery may become reoccluded.

The formation of fibrin-platelet clots in other parts of the circulatory system may be partially prevented through the use of anti-coagulants (such as heparin). Unfortunately, heparin has not been found to be universally effective in preventing reocclusion in myocardial infarction victims in which the degree of blood vessel occlusion (the degree of "stenosis") is greater than or equal to 70%, particularly in those patients with severe residual coronary stenosis.

If an individual has formed a fibrin-platelet clot prior to the availability of medical assistance, the clot may be dissolved through the use of thrombolytic agents. A thrombolytic agent is a medicament capable of lysing the fibrin-platelet thrombus, and thereby permitting blood to again flow through the affected blood vessel. Such agents include streptokinase, prourokinase, urokinase, and tissue-type plasminogen activator (Ganz, W. et al., *J. Amer. Coll. Cardiol.* 1:1247–1253 (1983); Rentrop, K. P. et al., *Amer. J. Cardiol.* 54:29E–31E (1984); Gold, H. K. et al., *Amer. J. Cardiol.* 53:122C–125C (1984)).

Treatment with thrombolytic agents can often successfully restore coronary blood flow rapidly enough to interrupt myocardial infarction. Unfortunately, the dissolved fibrin-platelet clot has been found to reform after cessation of such thrombolytic therapy in a substantial number of patients. This reformation may result in the reocclusion of the affected blood vessels, and is, therefore, of substantial concern (Gold, H. K. et al., *Amer. J. Cardiol.* 53:122C–125C (1984); Gold, H. K. et al., *Circulation* 68:I-50–I-54 (1983)). Thus, although streptokinase treatment has been found to be successful in dissolving fibrin clots in approximately 85% of studied cases, reocclusion of the affected vessels has been found to occur in approximately 25% of the patients examined. (Gold, H. K., et al., *Circulation*, 68:I50–I54 (1983)).

Tissue-type plasminogen activator (t-PA) is considered to be a more desirable thrombolytic agent than either streptokinase or urokinase because it displays greater (though not absolute) specificity for fibrin than does either of these agents (Verstrate, M., et al., *Lancet*, 1:142 (1985)). Tissue-type plasminogen activator (t-PA) is a clot-specific thrombolytic agent with a rapid disposition rate from plasma. Tissue-type plasminogen activator (t-PA) has been found to be an effective thrombolytic agent in patients with acute myocardial infarction, producing coronary reflow (i.e., decreasing stenosis) in 45–75 minutes in approximately 70% of patients studied (Gold, H. K. et al., *Circulation* 73:347–352 (1986)).

Tissue-type plasminogen activator is administered at an infusion at a rate of approximately 1–2 mg/kg patient weight/90 minutes. Because t-PA at high concentration is capable of breaking down fibrinogen, the use of higher dosages has been associated with an increased potential of general hemorrhage. Increased t-PA dosages have not been found to uniformly increase the rate of clot dissolution.

The benefit of employing t-PA is significantly offset by the spontaneous rate of acute reocclusion which follows the cessation of t-PA therapy. Gold, H. K. and coworkers have found that cessation of t-PA therapy resulted in reocclusion of affected blood vessels in approximately 45% of patients studied (*Circulation* 73:347–352 (1986)). Increased t-PA dosages have not been found to decrease the tendency for coronary artery reocclusion. Significantly, the possibility of thrombin clot reformation is closely related to the degree of residual coronary stenosis (i.e., the extent of blood vessel blockage). Thus, reocclusion is more probable in individuals in which high grade stenosis (i.e., greater than 70% quantitative stenosis or greater than 80% non-quantitative stenosis) has occurred. The reocclusion of blood vessels has been found to be inhibited by continued infusion of t-PA (Gold, H. K. et al., *Circulation* 73:347–352 (1986)). Unfortunately, the relatively short biological half-life of t-PA and the potential for increasing the tendency for severe bleeding in some patients may make continued infusion of t-PA impractical for many heart attack victims.

In summary, clinical investigations have shown that the dissolved thrombus frequently reforms following the cessation of t-PA infusion (Gold, H. K. et al., *Circulation* 73:347–352 (1986)), but that the frequency of such reocclusion can be minimized by providing a second ("maintenance") t-PA infusion of a substantially lower dose but for a substantially longer period. Heparin is currently recognized as the appropriate concomitant therapy for patients receiving such a maintenance infusion. The treatment of coronary artery thrombosis (clotting) with t-PA requires, therefore, a continuous infusion at a high rate in order to obtain rapid reperfusion, and a maintenance infusion at a lower dose to prevent reocclusion in patients with high grade residual stenosis.

B. Mechanism of Fibrin Clot Formation

Clots are composed of both fibrin and blood platelets in various ratios. The fundamental reaction in blood clotting involves the conversion of a soluble plasma protein (fibrinogen) into insoluble fibrin. The conversion of fibrinogen into fibrin is catalyzed by the enzyme, thrombin, which is a serine protease. The general mechanism of blood clot formation is reviewed by Ganong, W. F. (In: *Review of Medical Physiology,* 9th ed., Lange, Los Altos, Calif. pp. 411–414 (1979)). Platelets are disk-shaped structures present in blood. They contribute to clot formation by both their incorporation with fibrin into an insoluble mass and by their enhancement of the rate of fibrinogen to fibrin conversion. Platelets contribute to clot formation in myocardial infarction and are a major component of clots that reocclude coronary arteries that have been reperfused by treatment with a thrombolytic agent. The formation of the platelet aggregate depends upon an interaction between fibrinogen (and perhaps von Willebrand's factor or fibronectin) and a receptor molecule present on the surface of platelets. This platelet fibrinogen receptor has been found to be a complex of two membrane glycoproteins, termed GPIIb and GPIIIa (Nachman, R. L. et al., *J. Clin. Invest.* 69:263–269 (1982); Coller, B. S. et al., *J. Clin. Invest.* 72:325–338 (1983)). The specific role of the GPIIb/GPIIIa receptor complex was elucidated by Coller, B. S. and coworkers through their isolation of a murine monoclonal antibody (known as monoclonal antibody 10E5) found to be capable of binding to glycoproteins IIb and IIIa, and of completely blocking the binding of fibrinogen to platelets. In order to avoid potential complications due to the possibility that the monoclonal antibody's Fc fragment region might inhibit aggregation non-specifically, Coller, et al. used the F(ab')$_2$ fragment of the 10E5 antibody in their experiments. (Coller, B. S. et al., *J Clin. Invests.* 72:325–338 (1983)). The F(ab')$_2$ fragment of an antibody includes only those regions of the antibody which are responsible for the antibody's specificity and antigen-binding capacity. The nature of F(ab')$_2$ fragments and procedures for their preparation are disclosed by Eisen, H. N. (In: *Microbiology,* 3rd ed., Davis, B. D. et al., Harper & Row, New York, pp. 342–349 (1980)).

An additional monoclonal antibody (designated 7E3) was found to block the binding of fibrinogen to platelets, and to bind to GPIIb/GPIIIa (Coller, B. S., *J. Clin. Invest.,* 76:101–108 (1985)). This monoclonal antibody differed from antibody 10E5 in that it bound much more rapidly to activated platelets than to unactivated platelets and was capable of binding to canine as well as human platelets (Coller, B. S., *J. Clin. Invest.* 76:101–108 (1985); Coller, B. S. et al., *J. Lab. Clin. Med.,* 107:384–392 (1986); both of which references are incorporated by reference herein). The F(ab')$_2$ fragments of monoclonal antibody 7E3 were found to be capable of interfering with platelet aggregation, thus suggesting a potential therapeutic use in the treatment of thrombotic disease (Coller, B. S. et al., *Blood* 66:1456–1459 (1985)). The F(ab')$_2$ fragment of monoclonal antibody 7E3 was also found to be effective in blocking the accumulation of multiple layers of platelets without producing an unacceptable risk of hemorrhage, thus suggesting a potential use in avoiding the total occlusion of blood vessels which may occur in myocardial infarction and stroke (Coller, B. S. et al., *Blood* 66:1456–1459 (1985)).

C. Mechanism of Clot Lysis and Natural Inhibition Thereof

Clot lysis is mediated by plasmin in vivo. Under natural conditions, plasminogen is converted to plasmin by tissue plasminogen activator (t-PA). Activation occurs on the fibrin surface, thus confining proteolytic activity to the appropriate site. After plasmin is set free into the circulation, it is rapidly combined with natural inhibitors. Inactivation of plasmin is the final and necessary step in the process of protecting against undesirable proteolysis. Such plasmin inhibitors include alpha-2-antiplasmin, alpha-2-macroglobulin and alpha-1-antitrypsin, all glycoproteins. Alpha-2-antiplasmin has a much higher affinity for plasmin than alpha-2-macroglobulin and binds specifically to plasmin in a 1:1 ratio. The larger pool of alpha-macroglobulin acts as a reservoir inhibitor. Kane, K. K., *Ann. Clin. Lab. Sci.* 14:443–449 (1984). Thus, clot lysis by the administration of t-PA is limited by the rapid and irreversible inactivation of plasmin by plasmin inhibitors.

Alpha-2-antiplasmin has three functional domains: the reactive site for plasmin, the plasmin(ogen) or LBS-binding site [complementary to the LBS (lysine-binding site) of plasmin(ogen)], and the cross-linking site for fibrin. Mimuro, J., et al., *Blood* 69:446–453 (1987). Mimuro et al. disclose antibodies to alpha-2-antiplasmin, one of which (JPTI-1) was specific to the reactive site of alpha-2-antiplasmin and prevented formation of alpha-2-antiplasmin-plasmin complexes, thereby inhibiting antiplasmin activity. However, Mimuro et al. do not teach administration of the JPTI-1 antibody to enhance clot lysis. Other antibodies specific for alpha-2-antiplasmin are taught by Plow, E. F., et al., *J. Biol. Chem.* 255:2902–2906 (1980); Wimen, B., et al., *Scan. J. Clin. Lab. Invest.* 43:27–33 (1983); Hattey, E., et al., *Thromb. Res.* 45:485–495 (1987); Collen, U.S. Pat. No. 4,346,029 (1980); and Collen, U.S. Pat. No. 4,198,335 (1980).

D. Summary

In summary, a substantial goal of therapies aimed at treating myocardial infarction involves limiting necrosis by permitting early reperfusion and by preventing reocclusion. At present, this goal is partially achieved through the administration of thrombolytic agents capable of dissolving the potentially life-threatening fibrin-platelet clots. The potential benefit of employing such agents is, however, significantly offset by their lack of fibrin specificity (as in the case of streptokinase and urokinase), or by their relatively short biological half-life caused by plasmin inhibitors (which may result in reformation of the fibrin clot, and the accompanying reocclusion of the affected blood vessels). Hence, a need exists for an improvement in thrombolytic therapy which enhances clot lysis, while minimizing fibrinogen breakdown and preventing reocclusion of the affected coronary artery.

SUMMARY OF THE INVENTION

The present invention provides an improved thrombolytic therapy for the treatment of myocardial infarction, and blood clots within patients. The invention also relates to compositions and methods for treating myocardial infarction and blood clots comprising administration of a hapten-binding molecule capable of preventing the inhibition of plasmin in an amount sufficient to prevent such inhibition.

The invention also provides a method of treatment for myocardial infarction which comprises coadministering to a patient in need of such treatment:

(a) a hapten-binding molecule capable of preventing the inhibition of plasmin by a plasmin inhibitor in an amount sufficient to prevent such inhibition; and (b) a thrombolytic agent, in an amount sufficient to either (i) dissolve a fibrin-platelet clot or (ii) inhibit the formation of a fibrin-platelet clot; wherein the hapten-binding molecule (a) is different from the thrombolytic agent (b).

The invention additionally pertains to a kit useful for carrying out the above method being compartmentalized in close confinement to receive two or more container means therein, which comprises;

(1) a first container containing a therapeutically effective amount of the hapten-binding molecule (a); and (2) a second container containing a therapeutically effective amount of the thrombolytic agent (b).

DESCRIPTION OF THE PREFERRED EMBODIMENTS

Figure 1:
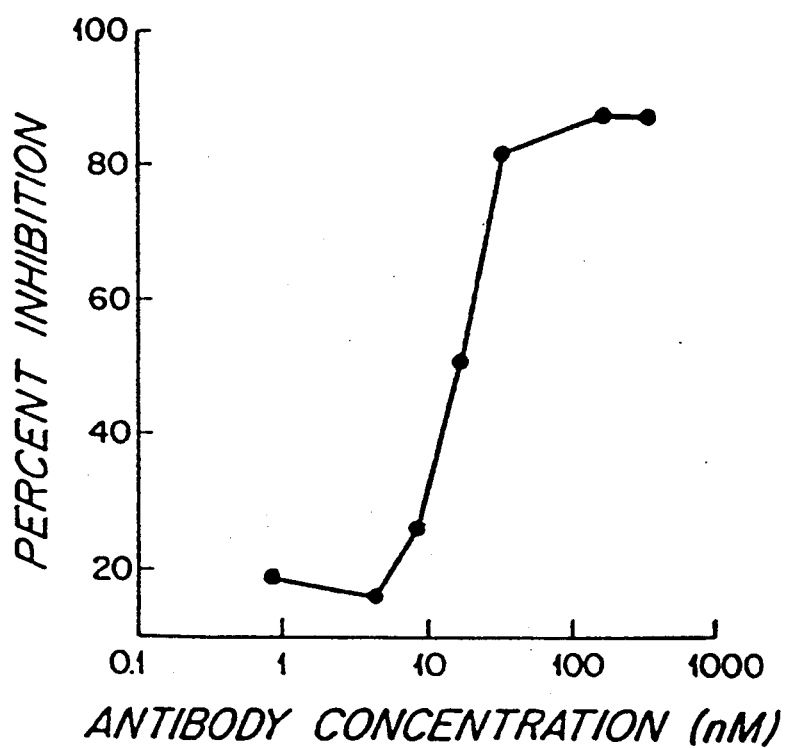
FIG. 1 depicts inhibition of α2AP by RWR. α2AP (final concentration, 20 nM) was mixed with various amounts of RWR and S-2251 (final concentration, 0.3 mM) for 2 hr at 25° C. Plasmin was added (final concentration, 100 nM) and the percentage of residual α2AP occurred at an antibody concentration of 14 nM.

The present invention is directed to a method for treating myocardial infarction and blood clots within a patient comprising administering a hapten-binding molecule capable of preventing the inhibition of plasmin, in an amount sufficient to prevent such inhibition.

The present invention also involves a treatment for myocardial infarction and blood clots within a patient which comprises coadministering a hapten-binding molecule and a thrombolytic agent to a recipient patient. A "hapten-binding molecule" is meant to refer to any molecule capable of binding to a plasmin inhibitor. Such molecules may include antibodies, antibody fragments (such as, for example, F(ab')2 or F(ab) molecules), as well as any ligand capable of binding to a plasmin inhibitor.

Blood clots which may be treated according to the methods of the invention include, but are not limited to pulmonary thromboembolism, deep venous thrombosis, cerebral embolism, renal vein and peripheral arterial thrombosis, and the like.

By the term "co-administration" is intended that each of the hapten-binding molecule and thrombolytic agent will be administered during a time frame wherein the respective periods of pharmacological activity overlap. The two agents may be administered simultaneously or sequentially.

The hapten-binding molecules of the present invention may be monoclonal antibodies or fragments thereof. It is preferable to employ the F(ab')2 fragment of such an antibody for this purpose, in order to minimize any immunological reaction caused by the Fc portion of the immunoglobulin. Procedures for preparing monoclonal antibodies are disclosed by Kaprowski, H. et al. (U.S. Pat. No. 4,172,124); and Kohler et al. (*Nature* 256:495-497 (1975)). The preparation of monoclonal antibodies capable of preventing the inhibition of plasmin are taught by Mimuro, J., et al., *Blood* 69:446-453 (1987) and described in the examples section of the present application.

As used herein, a "hapten" is a molecule capable of being bound by an antibody. In order to be used in accordance with the present invention, the hapten-binding molecule must be capable of binding to a plasmin inhibitor and thereby preventing such an inhibitor from forming inhibitor-plasmin complexes. Although any such hapten-binding molecule may be employed in accordance with the present invention, it is preferable to employ a hapten-binding molecule which is capable of binding to the plasmin binding site of alpha-2-antiplasmin. An especially preferred monoclonal antibody for this purpose is the antibody RWR described more fully below.

The term "thrombolytic agent" is meant to refer to any agent capable of either dissolving a fibrin-platelet clot, or inhibiting the formation of such a clot. Examples of thrombolytic agents include streptokinase, prourokinase, urokinase, and tissue-type plasminogen activator. Use of t-PA for these purposes is especially preferred. Although natural t-PA may be employed, it is preferable to employ recombinant t-PA. The invention may additionally employ hybrids, physiologically active fragments or mutant forms of the above thrombolytic agents. The term "tissue-type plasminogen activator" as used herein is intended to include such hybrids, fragments and mutants, as well as both naturally derived and recombinantly derived tissue-type plasminogen activator.

As stated, the methods of the invention comprise the administration of the hapten-binding molecule alone or in combination with a thrombolytic agent. When administered alone the molecule enhances in vivo thrombolysis by significantly augmenting clot lysis by endogenous plasminogen activators. Further, administration of the hapten-binding molecule does not increase fibrinogen consumption over that obtained with equivalent doses of t-PA alone. Thus, the present method of clot-specific inhibition of α2AP enhances the potency of the plasminogen activator and preserves its fibrin selectivity.

Alternatively, the hapten-binding molecule is administered with a thrombolytic agent. In this embodiment, the hapten-binding molecule and the thrombolytic agent of the present invention are intended to be co-administered to the recipient. It is preferable to provide the hapten-binding molecule to the patient prior to the administration of the thrombolytic agent. It is most preferable to provide the hapten-binding molecule 45 minutes, preferably 30 minutes, prior to the administration of the thrombolytic agent.

The hapten-binding molecule of the present invention is provided for the purpose of preventing the inhibition of plasmin by a plasmin inhibitor. Unexpectedly, it has been discovered that coadministration of the hapten-binding molecule together with a thrombolytic agent causes a synergistic effect, and thereby enhances clot lyses to a greater extent than would be expected if the effects of hapten-binding molecule administration and thrombolytic agent administration were merely additive.

The hapten-binding molecule of the present invention encompasses clot-specific inhibitors of α2AP. It is demonstrated that the combination of t-PA and the specific inhibitors, particularly monoclonal antibodies to α2AP, does not increase fibrinogen consumption over that obtained with equipotent doses of plasminogen activator alone. Further, clot-specific inhibition of α2AP enhances the potency of plasminogen activators and preserves fibrin selectivity. For agents such as urokinase, which is not selective for fibrin, a clot-specific inhibitor of alpha-PA would cause a similar, or more pronounced, enhancement in potency and lead to less fibrinogen consumption as well.

Thus, the inhibition of clot-bound α2AP enhances clot lysis by endogenous plasminogen activators. Further, when administered in combination with a thrombolytic agent, thrombolysis is significantly increased compared with the lysis achieved by equivalent doses of the thrombolytic agent alone. This increased lysis by the combination of the thrombolytic agent and α2AP inhibitor occurs without decreasing circulating fibrinogen or α2AP levels. The net result is a synergistic interaction between the two agents.

When used alone, an amount of hapten-binding molecule capable of preventing inhibition of plasmin and thereby enhancing clot lysis when provided to a patient is a "therapeutically effective" amount. In order to enhance clot lysis and prevent clot reformation, it is desirable to provide between 3 to 100 nmole of hapten-binding molecule per kilogram of patient weight. This dosage may be administered, in one embodiment, over a period of between 60 to 480 minutes, by continual intravenous infusion at a rate of 0.10–1.0 mg/kg min. Alternatively, it is possible to provide the hapten-binding molecule in an intravenously injectable bolus at a dose of between 3 to 100 nmole/kg, and most preferably between 3 to 6 nmole (of hapten-binding molecule) per kilogram of patient weight. If the hapten-binding molecule is provided in this manner, a single bolus is sufficient to prevent potential clot reformation. The hapten-binding molecule of the present invention may be dissolved in any physiologically tolerated liquid in order to prepare an injectable bolus. It is preferable to prepare such a bolus by dissolving the hapten-binding molecule in normal saline.

When the hapten-binding molecule capable of preventing inhibition of plasmin is co-administered with a thrombolytic agent, it is desirable to provide 3 to 6 nmole of hapten-binding molecule per kilogram of patient weight. This dosage may be administered, in one embodiment, over a period of 60 to 480 minutes, by continuous intravenous infusion. Alternatively, it is possible to provide the hapten-binding molecule in an intravenously injectable bolus at a dose of between 3 to 6 nmole/kg, and most preferably between 1 to 3 nmole/kg of patient weight. An amount of thrombolytic agent capable of causing such lysis is a "therapeutically effective" amount. The thrombolytic agent of the present invention is preferably provided at a dose of between 0.5 to 1.0 mg per kg of patient weight. In one embodiment, the thrombolytic agent is provided over a prolonged period (i.e., from about 180 to about 1440 minutes). In a preferred embodiment, the thrombolytic agent of the present invention is provided as an intravenously injected bolus containing between 0.5 to 1.0 mg/kg, and most preferably between 0.5 to 0.75 mg/kg. The thrombolytic agent of the present invention may be dissolved in any physiologically tolerated liquid in order to prepare an injectable bolus. It is, however, preferable to prepare such a bolus by dissolving the thrombolytic agent in normal saline.

A patient treated according to the preferred embodiment will, therefore, receive an intravenously injected bolus of the hapten-binding molecule in combination with an intravenously injected bolus of the thrombolytic agent. This preferred treatment minimizes the amount of t-PA required for thrombolysis, thus reducing the extent of fibrinogen breakdown and lessening any tendency for general hemorrhage. Importantly, the use of the preferred treatment results in the dissolution of the occluding thrombus at a rate which greatly exceeds the rate of thrombus dissolution when either the hapten-binding molecule or the thrombolytic agent is provided by infusion. Additionally, the risk of reocclusion is substantially reduced.

In previous models of fibrinolysis (3), the chief role assigned to α2AP has been to inactivate circulating plasmin and prevent a systemic lytic state. Thus, it may be surprising that an α2AP inhibitor can increase clot lysis without increasing fibrinogenolysis. As demonstrated, the inhibitory subject antibodies, although selected for binding to free α2AP, demonstrate better inhibition of fibrin-bound α2AP. Since the subject antibodies augment clot lysis by a fibrin-selective agent such as t-PA as well as that by the non-selective activators urokinase and streptokinase, it appears that fibrin-bound α2AP plays a critical role in determining the rate of lysis by any exogenous plasminogen activator.

In particular, results showed that antibody RWR appeared to have a greater effect on the lytic potency of urokinase and t-PA than on that of streptokinase. This difference may be due to the fact that α2AP is a slow inhibitor of both urokinase and t-PA but has no significant effect on the strep-tokinase-plasmin complex. Further, α2AP inhibition augmented the fibrinolytic potency of urokinase more than it did t-PA. This is consistent with previous findings that t-PA is relatively less sensitive to the inhibitory effects of α2AP, probably because of its fibrin binding ability and preferential activation of fibrin-bound plasminogen (Matsuo, O., et al., Thromb. Haemost. 45:225–229 (1981)). The antibody's pronounced enhancement of urokinase-induced clot lysis also magnified its fibrinogen-sparing effects with this plasminogen activator.

These unexpected findings are important because it had previously not been possible to accelerate the rate of clot lysis without increasing the tendency to hemorrhage. The preferred embodiment, therefore, provides a method of treatment in which the administration of a bolus of a hapten-binding molecule in combination with the administration of a bolus of a thrombolytic agent are capable of dissolving an occluding thrombus at a faster rate than can be obtained when either compound is administered alone. Moreover, the preferred embodiment accomplishes this goal while minimizing both fibrinogen breakdown and the risk of reocclusion. Thus, the combination of agents can significantly increase the potency and specificity of thrombolytic therapy.

As would be apparent to one of ordinary skill in the art, the required dosage of the anti-hapten binding molecule or thrombolytic agent will depend upon the severity of the condition of the patient, and upon such criteria as the patient's height, weight, sex, age, and medical history.

The hapten-binding molecule or thrombolytic agent of the present invention can be formulated according to known methods to prepare pharmaceutically useful compositions, such as by admixture with a pharmaceutically acceptable carrier vehicle. Suitable vehicles and their formulation are described, for example, in Remington's Pharmaceutical Sciences (16th Ed., Osol, A.

(ed.), Mack, Easton Pa. (1980)). In order to form a pharmaceutically acceptable composition suitable for effective administration, such compositions will contain an effective amount of the hapten-binding molecule or thrombolytic agent, either alone, or with a suitable amount of carrier vehicle.

Additional pharmaceutical methods may be employed to control the duration of action. Controlled release preparations may be achieved by the use of polymers to complex or absorb the hapten-binding molecule or thrombolytic agents of the present invention, The control led delivery may be exercised by selecting appropriate macromolecules (for example, polyesters, polyamino acids, polyvinyl pyrrolidone, ethylenevinylacetate, methylcellulose, carboxymethylcellulose, or protamine sulfate). The rate of drug release may also be controlled by altering the concentration of such macromolecules. Another possible method for controlling the duration of action comprises incorporating the therapeutic agents into particles of a polymeric substance such as polyesters, polyamino acids, hydrogels, poly(-lactic acid) or ethylene vinylacetate copolymers. Alternatively, it is possible to entrap the therapeutic agents in microcapsules prepared, for example, by coacervation techniques or by interfacial polymerization, for example, by the use of hydroxymethylcellulose or gelatin-microcapsules or poly(methylmethacrylate) microcapsules, respectively, or in a colloid drug delivery system, for example, liposomes, albumin microspheres, microemulsions, nanoparticles, nanocapsules, or in macroemulsions. Such teachings are disclosed in Remington's Pharmaceutical Sciences (1980 ).

The thrombolytic agent or hapten-binding molecule may be provided to a patient by means well known in the art. Such means of introduction include oral means, intranasal means, subcutaneous means, intramuscular means, intravenous means, intra-arterial means, or parenteral means. In the most preferred method of treatment for myocardial infarction, a patient is provided with a bolus (intravenously injected) containing between 0.5 to 1.0 mg/kg.

Generally, the results reported herein demonstrate that an inhibitor, particularly a monoclonal antibody, can be used to augment the catalytic function of an enzyme by neutralizing an inhibitor of that enzyme. This approach can be applied to biological processes which are tightly governed by inhibitors. Because coagulation is a finely balanced system in which the effects of enzymes (generally serine proteases) are pitted against the effects of inhibitors, frequently serpines (serine protease inhibitors) pathological alterations in clotting can be treated by augmenting enzyme activity or by neutralizing an inhibitor.

Having now generally described this invention, the same will be better understood by reference to certain specific examples which are included herein for purposes of illustration only, and are not intended to be limiting of the invention, unless specified.

EXAMPLE 1

Preparation of an Antibody Directed to Alpha-2-antiplasmin

A. Materials

Aprotinin and Protein-A Sepharose were purchased from Sigma (St. Louis, Mo.). S2251 (H-D-Valyl-L-leucyl-L-lysine-p-nitroanilide dihydrochloride) was obtained from Helena Labs (Beaumont, Tex.). Human alpha-2-antiplasmin ($\alpha$2AP) was obtained from American Diagnostica, Inc. (Greenwich, Conn.). PD-10 columns were purchased from Pharmacia (Uppsala, Sweden). Microtiter plates were obtained from Becton Dickinson Labware (Oxnard, Calif.). Affinity purified goat anti-mouse (Fab')2 IgG was obtained from Cappel Labs (Cochranville, Pa.). A murine antibody isotyping kit was purchased from Boehringer Mannheim (Indianapolis, Id.).

B. Preparation of Proteins $\alpha$2AP was purified from multidonor frozen plasma by affinity chromatography as described by Wiman (Wiman, B., Method. Enzymol. 80:395–408 (1981)) followed by fast protein liquid chromatography on a Superose-12 column. This purification process yielded a single band on SDS-PAGE (Laemmli, V. K., Nature 227:680–685 (1970)). Plasminogen was isolated from plasma according to the protocol of Deutsch & Mertz (Deutsch, D. G., et al., Science 170, 1095–1096 (1970)) and activated with urokinase (Wiman, B., Method. Enzymol. 80:395–408 (1981). Determinations of $\alpha$2AP and plasminogen concentrations were based on absorption coefficients ($A_{280nm}^{1cm}$) for a 1% solution of 7.03 and 17.0, respectively (Moroi, M., et al., J. Biol. Chem. 251:5956–5965 (1976); Robbins, K. C., et al., J. Biol. Chem. 240:541–550 (1965)).

C. Preparation of Murine Monoclonal Antibodies Specific for Alpha-2-antiplasmin A/J mice were immunized i.p. and s.c. with 10 $\mu$g of human $\alpha$2AP in Complete Freund's Adjuvant. The mice were boosted 1 month later with 2 $\mu$g of protein in Incomplete Freund's Adjuvant. Two months after initial immunization, the mice were bled from a tail vein and the titres of antibody were determined. The mouse showing the highest titre was hyperimmunized with 5 $\mu$g i.v. (aqueous) and 10 $\mu$g i.p. of $\alpha$2AP in Incomplete Freund's Adjuvant four days prior, and 5 $\mu$g (aqueous) i.v. 3 days prior to fusion. Splenocytes and murine SP2/O cells were fused as described (Kohler et al., supra). Hybridomas were selected by a solid phase radioimmunoassay for $\alpha$2AP immobilized in wells of polyvinyl chloride microtiter plates. Specifically bound antibody was detected using affinity purified, goat anti-mouse F(ab')2 IgG. Twenty-one hybridomas specifically bound antigen. These hybridomas were subcloned to monoclonality by limiting dilution. Seven hybridomas were expanded into ascites using conventional techniques. Antibody was isolated from filtered ascites using affinity chromatography with Protein-A sepharose.

Isotyping was performed using a rabbit anti-mouse, anti-idiotypic antibodies coupled to peroxidase.

One particular hybridoma which produced an antibody (RWR) specific for alpha-2-antiplasmin of the isotype IgGl-K.

D. Characterization of the Antibody

Of 21 monoclonal antibodies obtained from the fusion, 7 were selected because of their binding in a solid-phase radioimmunoassay and expanded into ascites. After purification by Protein-A affinity chromatography, the antibodies were tested for their ability to inhibit the inactivation of human $\alpha$2AP by plasmin. One of these antibodies, (Ig$\gamma_1$-$\kappa$ serotype), showed a dose-related inhibition of the interaction between $\alpha$2AP and plasmin (FIG. 1) achieving 50% inhibition of $\alpha$2AP at a concentration of 14 nM or at a 0.7:1 molar ratio of RWR to α2AP.

EXAMPLE 2

Inhibition of Alpha-2-antiplasmin by RWR

A. Materials and Methods

Iodination of proteins was performed using the Iodogen method. Fraker, P. J. and Speck, J. C., *Biochem. Biophys. Res. Comm.* 80:849–857 (1978). The specific activity of RWR was 20.0 µCi/µg.

B. Inhibition Studies

Inhibition studies were of several types. First, a chromogenic substrate assay was used to test the ability of RWR to inhibit the inactivation of plasmin by antiplasmin. Using a previously described assay (Wiman, B. *Meth. Enzymol.* 80:1395–1403 (1981)) format, a standard curve was constructed for antiplasmin activity as described. Antiplasmin (0 to 25 nM) was mixed with 0.3 mM S2251 and plasmin (100 nM) in 0.1M, pH 7.3 phosphate buffer to a total of 1000 µl. The rate of change of optical density at 405 nanometers was automatically recorded every 10 seconds on a Hewlett-Packard 8451A spectrophotometer. A standard curve was constructed which related antiplasmin concentration to the rate of product formation in a linear fashion (r=0.98). Next, antiplasmin (25 nM) was mixed with RWR (0.875 to 350 nM) and incubated with 0.3 nM S2251 in 0.1M, pH 7.3 phosphate buffer for 2 hours at 25° C. Plasmin (100 nM) was quickly added and the optical density recorded. The rate of change of optical density was used to calculate the amount of inhibition of antiplasmin activity by a given level of antibody.

Figure 2:
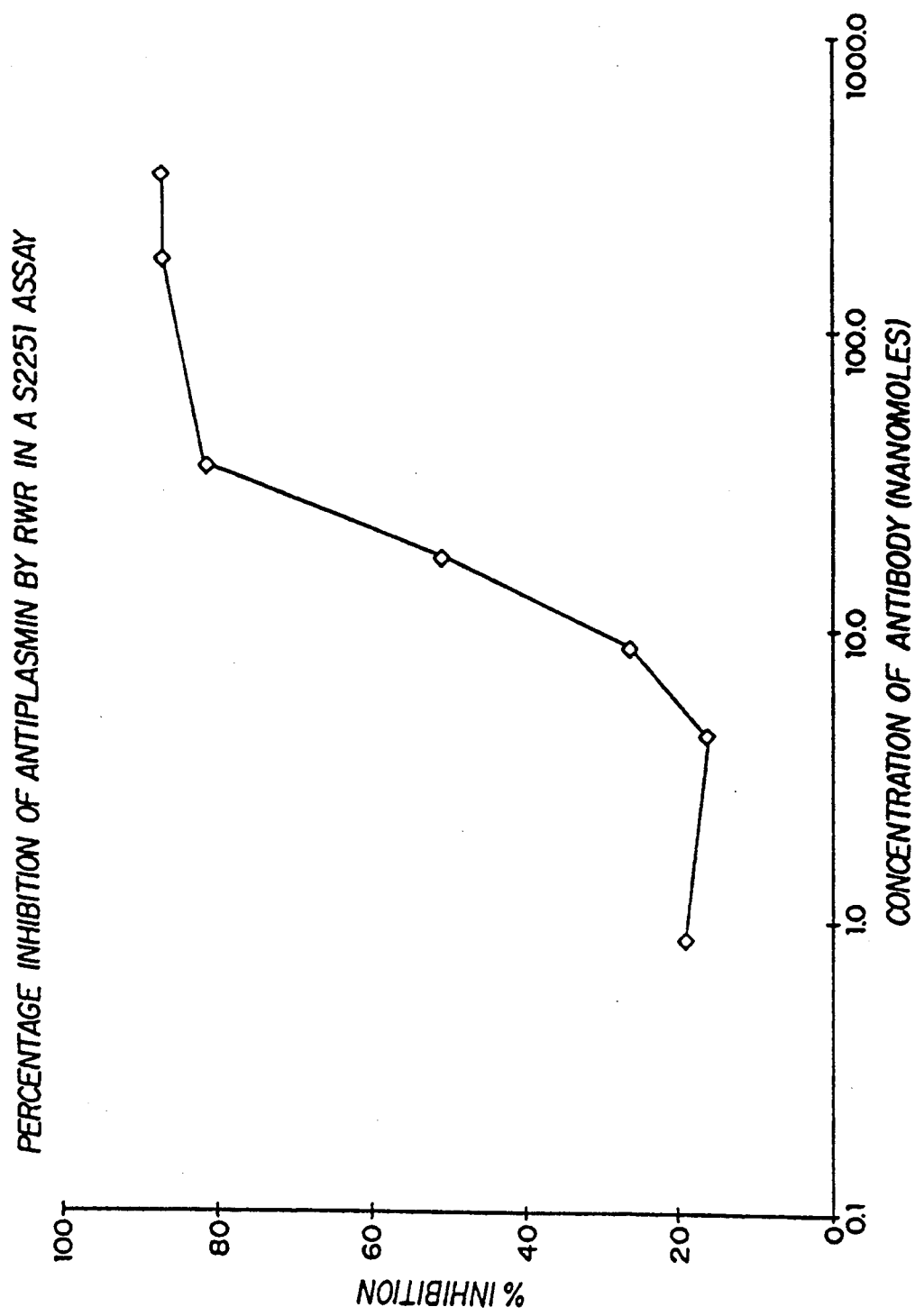
FIG. 2 depicts a graph of the percent inhibition of antiplasmin as a function of RWR concentration.

As shown in FIG. 2, 55% inhibition of alpha-2-antiplasmin occurred at an antibody concentration of 20 nmole. Immunoblotting under nondenaturing conditions showed that RWR binds the 70,000 Mr species of α2AP and not the 55,000 Mr, non-plasminogen binding form. In addition, RWR did not appreciably bind to denatured or reduced forms of α2AP.

C. Antibody Binding

Fresh-frozen human plasma (100 µL) pooled from 4 random donors was mixed with an 100-µL solution of thrombin (1 U/mL) and calcium chloride (4 mM) in 50 mM Tris-buffered saline, pH 7.4, in 75×12-mm test tubes and incubated in a water bath for 2 h at 37° C. The clots were then treated with 100 µL of 0.1% iodoacetamide for 15 min, washed with 2 mL of 10 mM phosphate-buffered saline, pH 7.4, and compressed to extrude unbound proteins. After the clots were incubated overnight at 4° C. with monoclonal antibody RWR or a control antibody of the same isotype [antidigoxin antibody 40-160 (Mudgett-Hunter et al., *Mol. Immunol.* 22:477–488 (1985))], they were washed again with buffer and incubated with $^{125}$I-labeled GAMFab (100,000 cpm) for 1 h at room temperature. After an additional washing, the amount of antibody bound to the plasma clots was determined by gamma emission counting.

D. Time-related Lysis of Plasma Clots t-PA

Fifty µL of fresh-frozen, multidonor human plasma was mixed with trace amounts of $^{125}$I-labeled fibrinogen in 75×12-mm test tubes and clotted with a 50-µL solution of thrombin (1 U/mL) and CaCl$_2$ (50 mM) in 10 mM Tris-buffered saline, pH 7.4, in a 37° C. water bath for 2 h. The clots were counted in a gamma counter and RWR (0 or 250 nM), control antidigoxin 40-160 (0 or 250 nM), or t-PA (0 or 1 IU) were added to the clot in each tube. The total volume of each tube was brought up to 1 mL with 10 mM Tris, 0.11M NaCl, and 2 mM CaCl$_2$. At various intervals a 200-µl aliquot of supernatant was sampled and gamma-counted. The percentage lysis was computed from the initial radioactivity in the clot and the radioactivity released into the supernatant as soluble fibrin degradation products.

To study the effect of RWR on lysis by "endogenous" plasminogen activator, radiolabeled plasma clots were made as just described. Then RWR or the control antibody (500 nM, final) were added to the clots in each tube (in quadruplicate) and the total volume was brought up to 500 µL with Tris-buffered saline azide containing 2 mM CaCl$_2$. At various intervals an aliquot of supernatant was sampled and gamma counted to compute the percent lysis.

EXAMPLE 3

Enhancement of Clot Lysis with RWR or t-PA

A. Materials and Methods

Fresh-frozen, pooled (8 random donors), human plasma was used. To make clots, plasma was mixed with small amounts of fibrin. In 75×12 mm test tubes, 25 µl of plasma was vortexed with 25 µl solution of bovine thrombin (1 U/ml) and calcium chloride (4 mM) in 50 mM Tris-buffered saline pH 7.4. Tubes were placed in a 37° C. oscillating water bath to facilitate clotting. The tubes were then counted in a gamma counter to determine the baseline amount of 125-I labeled fibrin incorporated into the clot. Varying amounts of RWR and plasmin were added to each tube clot and the total volume was brought up to 1 ml with 50 mMole Tris, 0.11M NaCl, and 2 mMole CaCl$_2$. The percentage lysis was determined by measurement of the release of radiolabeled, soluble fibrin peptide. At the indicated time intervals, the supernatant was sampled without replacement and counted. Experiments were done in triplicate and percentage lysis was calculated using the following formula:

Cumulative percentage lysis at time
$i = L_i = 100(S_i * TV_i / SV_i + \Sigma_{0 max(0, i-1)} S_i)$ where $S_i$=supernatant counts, $TV_i$=total volume remaining in the tube at time i, $SV_i$=volume of supernatant sampled at time i, and $\Sigma S_i$ represents the sum of previous supernatant samples taken without replacement.

Figure 3:
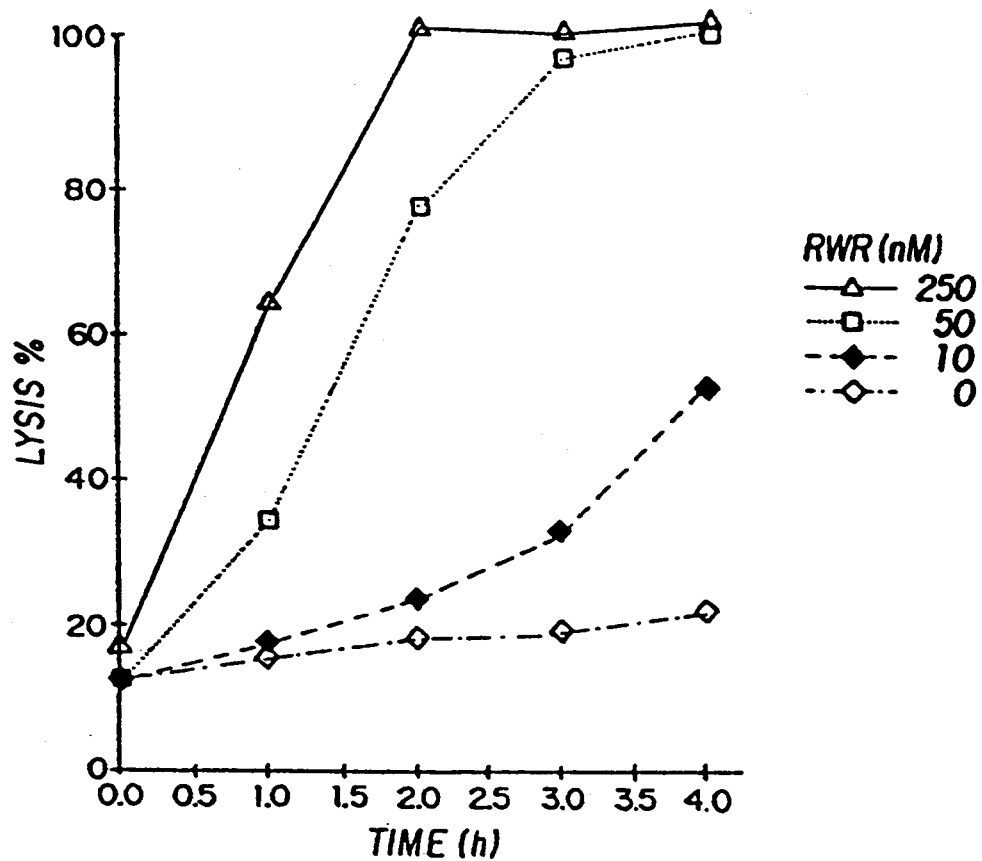
FIG. 3 depicts a graph of the percent clot lysis by plasmin as a function of RWR concentration.

FIG. 3 depicts a graph of percent plasma clot lysis as a function of RWR concentration. As can be seen from FIG. 3, RWR causes a dose-related significant enhancement of clot lysis by plasmin. Significant clot lysis was observed even at a low concentration of 10 nmole (molar ratio of Mab:α2AP of 0.4:1) over 4 hours. Thus, partial inhibition of α2AP results in a significant increase in fibrinolysis by plasmin. As the concentration of RWR is increased, substantially greater clot lysis was observed.

B. Binding of Antibody to α2AP Cross-linked to Plasma Clots

Figure 4:
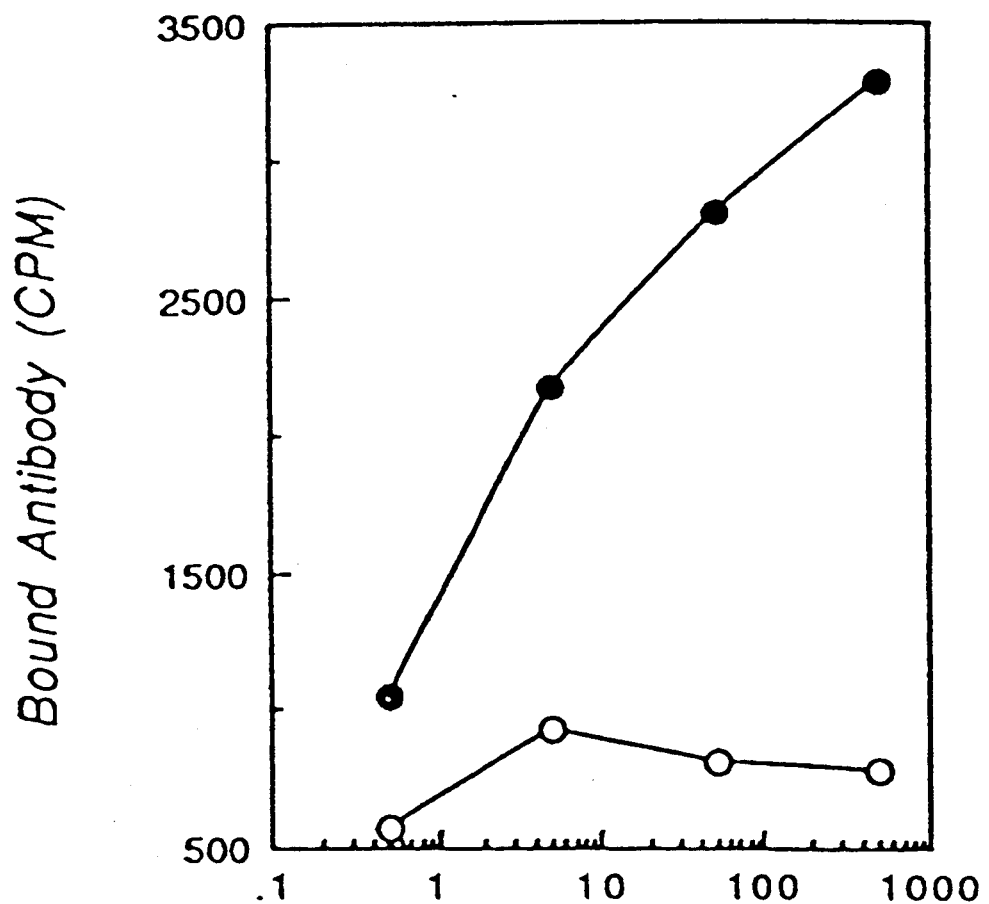
FIG. 4 depicts binding RWR to α2AP cross-linked to fibrin (4) in a plasma clot assay. Washed plasma clots were incubated with various concentrations of RWR (solid circles) or an anti-digoxin control antibody (open circles) of the same isotype (15). After the washing, monoclonal antibody bound to the clot was detected with $^{125}$I-labeled GAMFab. The means of triplicate observations are shown.

Because antibody RWR was capable of binding to and inhibiting α2AP in solution, it was tested for the ability to bind to α2AP that had been cross-linked to fibrin by activated Factor XIII. After plasma clots had been treated with 0.1% iodoacetamide to inhibit activated Factor XIII (which catalyzes the reversible cross-linking of α2AP to fibrin (Mimuro et al., *J. Clin. Invest.* 77:1006–1013 (1986)), they were washed and incubated with various amounts of RWR or a control antibody of the same isotype [antidigoxin monoclonal antibody 40–160 (Mudgett-Hunter et al., Supra)]. Antibody bound to the plasma clots was detected with $^{125}$I-labeled GaMFab. FIG. 4 shows that, compared with the control antibody, bound in a dose-dependent fashion to α2AP cross-linked to the fibrin clot.

C. Enhancement of "Endogenous Lysis" by Antibody RWR

Figure 5:
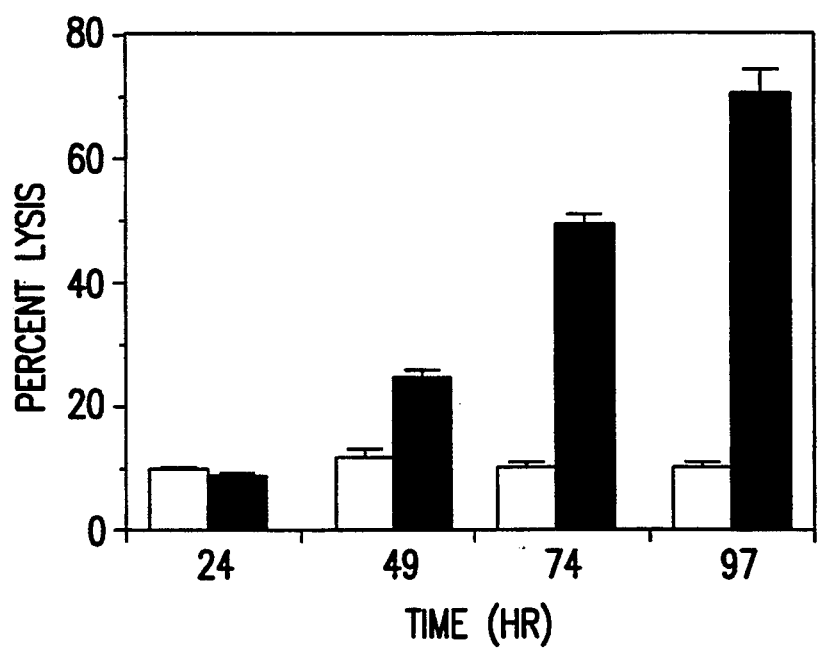
FIG. 5 depicts enhancement of "endogenous" clot lysis by monoclonal antibody RWR. Plasma was clotted with trace amount of $^{125}$I-labeled fibrinogen. The clots were incubated with RWR (stippled bars) or a control antibody (anti-digoxin 40–160; open bars). At the indicated times, the percentage clot lysis was determined. The means and SEMs of quadruplicate observations are shown.

The clinical hallmark of human α2AP deficiency is the spontaneous lysis of blood clots in vivo (Aoki et al., *J. Clin. Invest.* 63:877–884 (1979)). This apparently results from the uninhibited action of plasmin generated by endogenous plasminogen activator (Miles et al., *Blood* 59:1246–1251 (1982)). Because RWR binds to soluble and fibrin-cross-linked α2AP, the ability of to RWR reproduce this spontaneous clot lysis was tested. FIG. 5 shows that, compared with the control antibody (antidigoxin 40–160), RWR caused increasing "endogenous" or spontaneous lysis. Thus RWR reproduced the spontaneous clot lysis seen in human deficiency.

D. Clot Lysis by t-PA and RWR

Figure 6:
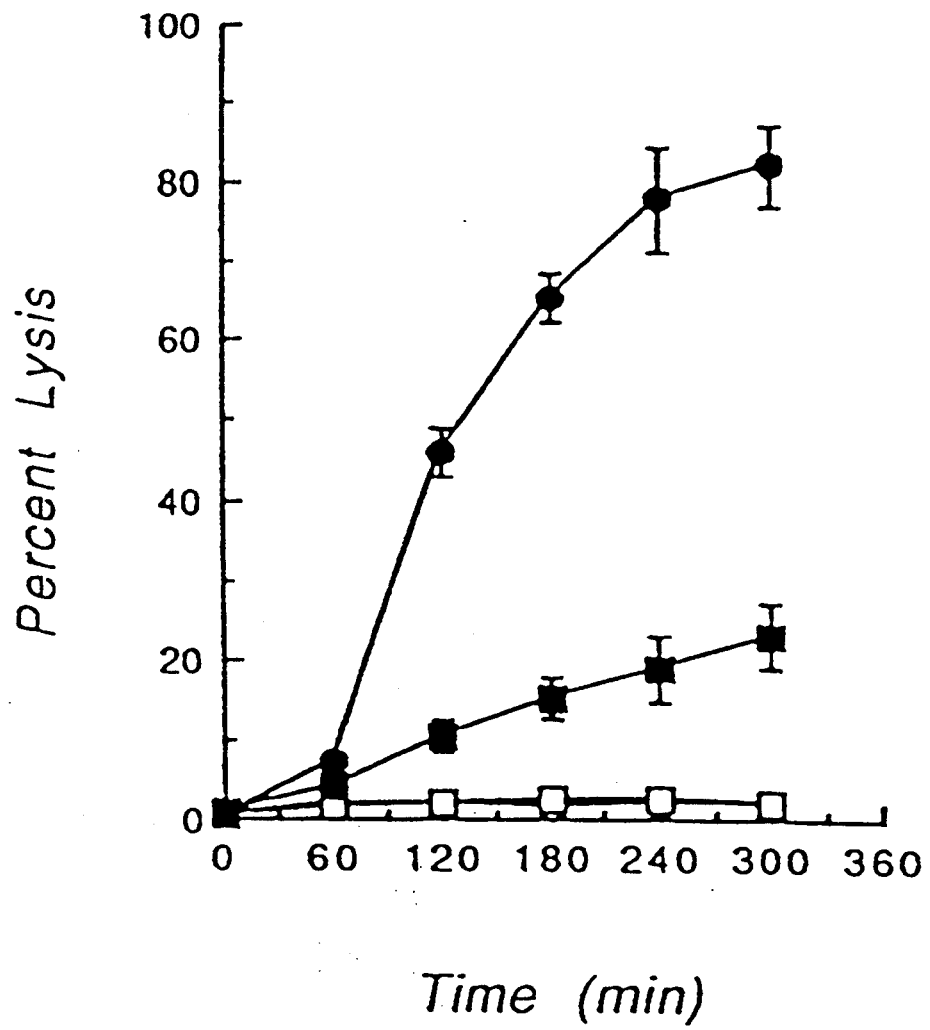
FIG. 6 depicts plasma clot lysis by t-PA and monoclonal antibody RWR or a control antibody. Clots were incubated with a 250 nM concentration of RWR (open circles), control antibody alone (open squares) (note that these two curves are superimposed), or a 250 nM concentration of RWR plus 5 IU of t-PA (solid circles) or control antibody plus 5 IU of t-PA (solid squares). At the indicated times, the percentage clot lysis was determined. The data represent the means and SEMs of observations in triplicate.

Since t-PA preferentially activates fibrin-bound plasminogen to plasmin, and fibrin-bound plasmin is relatively resistant to the inhibitory effects of α2AP (Matsuo et al., *Thromb. Haemort.* 45:225–229 (1981)), it might be expected that clot lysis by t-PA would not be significantly affected by an α2AP inhibitor. To test this hypothesis, the rate of fibrinolysis was measured in plasma clots treated with RWR or a control antibody alone, or RWR or the control antibody in combination with t-PA. During the relatively brief time of this experiment (5 h, cf. FIG. 5), RWR alone did not cause more lysis than the control antibody alone (FIG. 6). The combination of the control antibody and t-PA caused slightly more clot lysis. However, RWR and t-PA in combination almost completely lysed the clot. The marked enhancement of clot lysis by the combination of RWR and t-PA suggested that the two agents interact synergistically.

EXAMPLE 4

Determination of the Synergistic Effect on Clot Lysis by RWR and t-PA

Figure 7A:
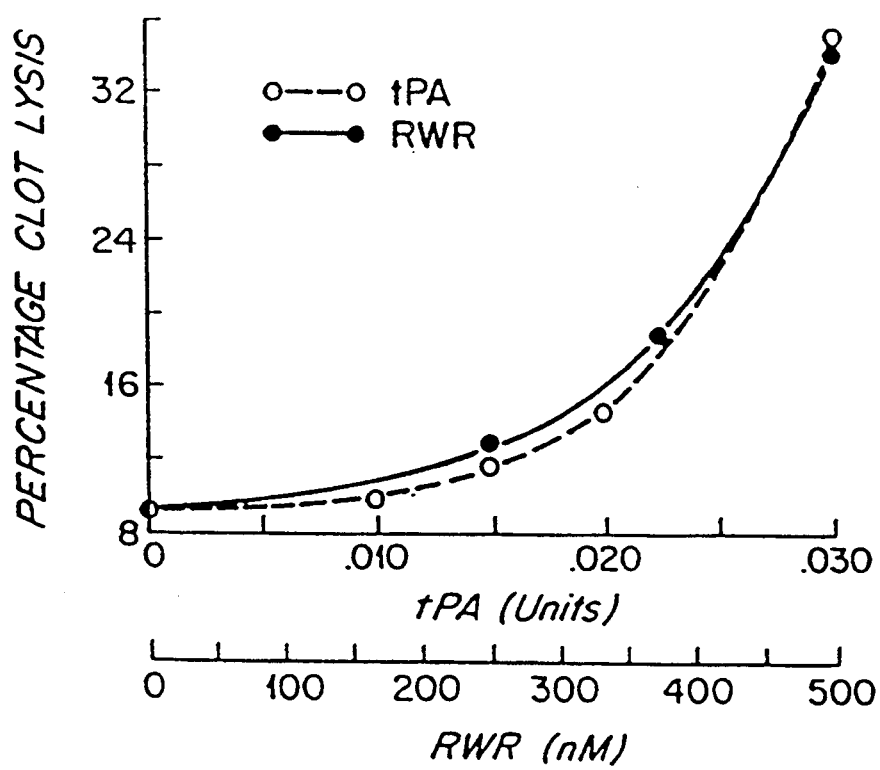
FIG. 7 depicts the synergistic effects of t-PA and RWR on plasma clot lysis. To determine the effect of combinations of t-PA and RWR on lysis, we constructed an isobole as recommended by previous studies (Loewe, S., *Pharmacol. Rev.* 9:237–242 (1957); Berenbaum, M. C., *Adv. Cancer Res.* 35:269–335 (1981); Berenbaum, M. C., *J. Theor. Biol.* 114:413–431 (1985)). (A) First, isoeffective doses of t-PA and RWR were determined. In these studies, t-PA (0.03 IU/ml; 1.2×10$^{-3}$ nM) (open circles) and 500 nM RWR (solid circles) produced an equivalent percent lysis (35.5±3.1 and 34.3±5.1; mean±SEM, observations in triplicate). (B) (Inset) Hypothetical isobole [cf. Berenbaum (Berenbaum, M. C., *J. Theor. Biol.* 114:413–431 (1985))], demonstrating synergy, additivity, and antagonism (see Results for explanation). (B) Experimental isobole illustrating the interaction between t-PA and RWR in clot lysis. Dose combinations of RWR and t-PA that produced mean clot lysis equivalent to lysis with these agents alone are indicated by solid circles. Open circles denote dose combinations showing still higher mean lysis (40–100%). Compared with each agent alone, combinations of RWR and t-PA are strongly synergistic.
Figure 7B:
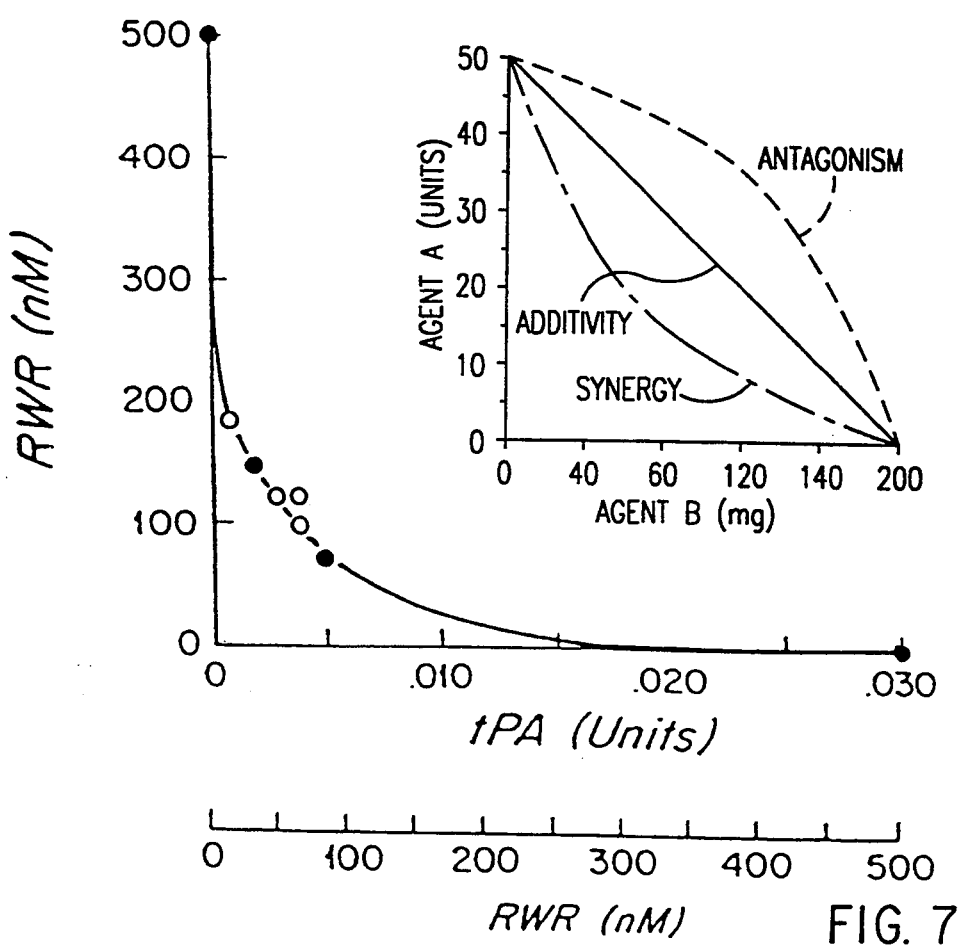

The synergism between t-PA and RWR was studied as previously defined (Loewe, S., *Pharmacol. Rev.* 237–242 (1957); Berenbaum, M. C., *Adv. Cancer* 35:237–242 (1981)). This analysis requires that the dose-response curves for both agents be constructed (Berenbaum, M. C., *J. Theor. Biol.* 114:413–421 (1985)). Using this, doses of t-PA and RWR are selected which are isoeffective. Fractional doses of the two agents are then combined and their joint effect on clot lysis is determined. An isobole is constructed which graphs the amount of each agent, alone or in combination, that produces an equivalent amount of lysis in a given period of time. The graphical determination of synergy, additivity, and antagonism is shown in FIG. 7B.

Alternatively, these types of interactions may be defined algebraically. Given isoeffective doses of each separate agent A & B, the isoeffective fractional doses of each agent in combination ($a_i$ and $b_i$) can be characterized as: synergistic if $a_i/A + b_i/B < 1$, additive if $a_i/A + B_i/B = 1$, or antagonistic if $a_i/A + B_i/B > 1$.

To determine this empirically, various amounts of t-PA and RWR were added separately and in combination to test tube labeled clots (in triplicate as described below). Then the mean percentage lysis was determined as indicated.

Figure 8:
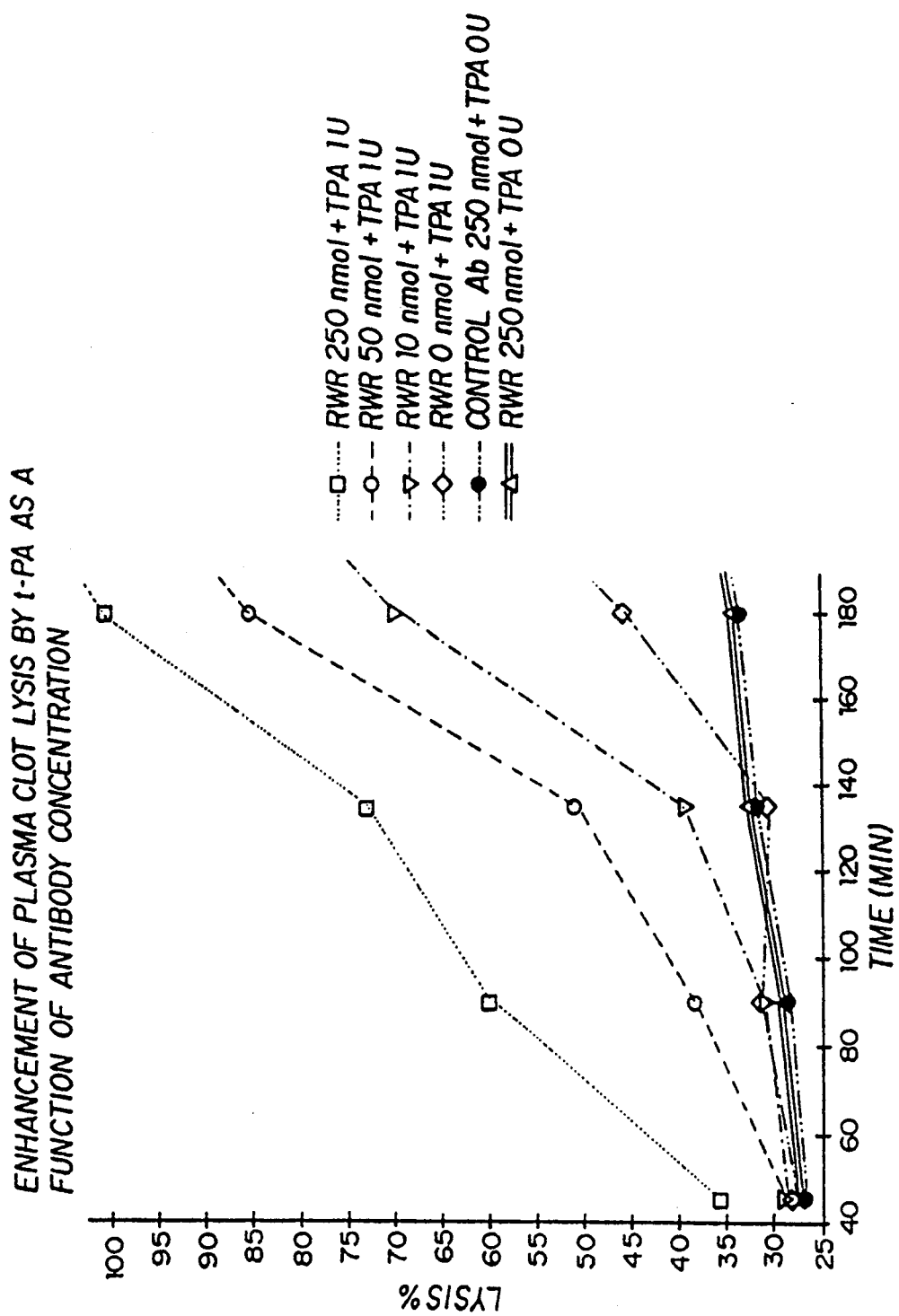
FIG. 8 depicts a graph of the percent clot lysis by t-PA as a function of RWR concentration.
Figure 9:
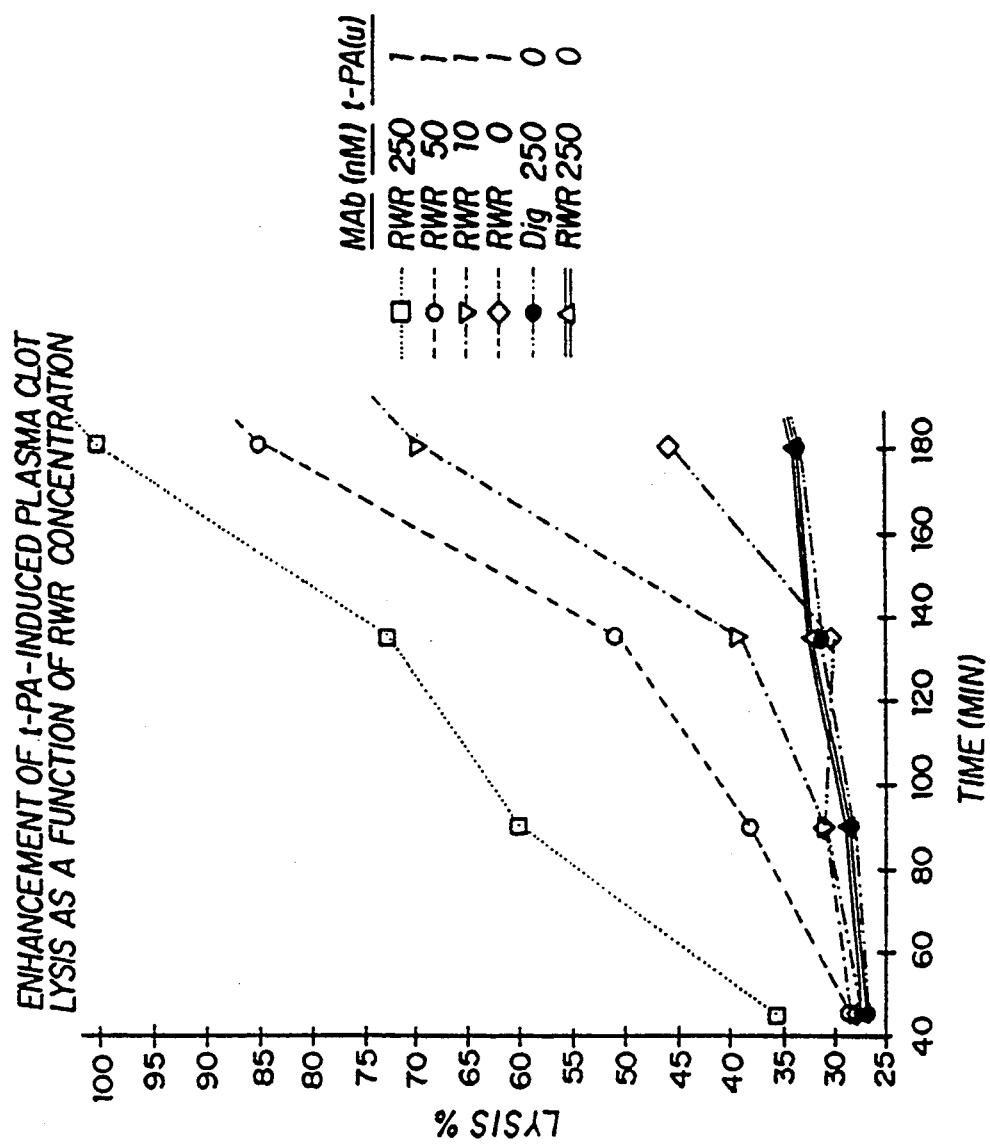
FIG. 9 depicts a graph of the percent clot lysis, wherein RWR is added before or after clotting, as a function of t-PA concentration.

Fresh-frozen plasma was mixed with 125-I labeled fibrinogen and clotted. Then varying amounts of RWR (0 to 250 mmol, final) or control (anti-digoxin) antibody (0 or 250 nmol, final) were added to tubes containing 0 or 1 unit of t-PA. Tubes were incubated at 37° C. and the percentage lysis was determined by the release of radiolabeled fibrin peptides. In control clots, in the time indicated, RWR alone was not different from a control antibody alone-an anti-digoxin Mab 40–160 (Mudgett-Hunter, M., et al., *Mol. Immunol.* 22:477–488 (1985))—in the amount of lysis induced without t-PA. However, in the presence of t-PA, RWR shows a dose-related enhancement of clot lysis which is greater than that seen in clots tested with t-PA alone. FIG. 8 shows the effect of varying concentrations of t-PA and RWR on clot lysis, Approximately 30% of antiplasmin is cross-linked to fibrin by Factor 13, If cross-linked antiplasmin is not available to the antibody for binding, this would significantly decrease the antibody's effect on the rate of clot lysis. As such clots formed with antibody already bound to α2AP should lyse more quickly than those to which the antibody was added after cloning, i.e., after the cross-linking of α2AP to fibrin. To test this hypothesis, the time-related lysis in clots formed after preincubation of the plasma with RWR was compared to that of formed clots to which RWR was subsequently added (FIG. 9).

Fresh-frozen plasma was mixed with radiolabeled fibrinogen. Then RWR (25 nmole, final) was mixed with plasma and clotted. In other experiments, RWR was added to already formed plasma clots. Clots were subsequently incubated in buffer for 24 hours at 4° C. Then t-PA (0, 0.1, or 1 u) was added and the clots were incubated at 37° C. The rate of lysis was determined as described above. It can be seen in FIG. 9 that there is only a slight increase in the rate of lysis for clots which were exposed to RWR prior to formation. This suggests that antiplasmin is functionally accessible to the MAb in cross-linked fibrin.

Figure 11:
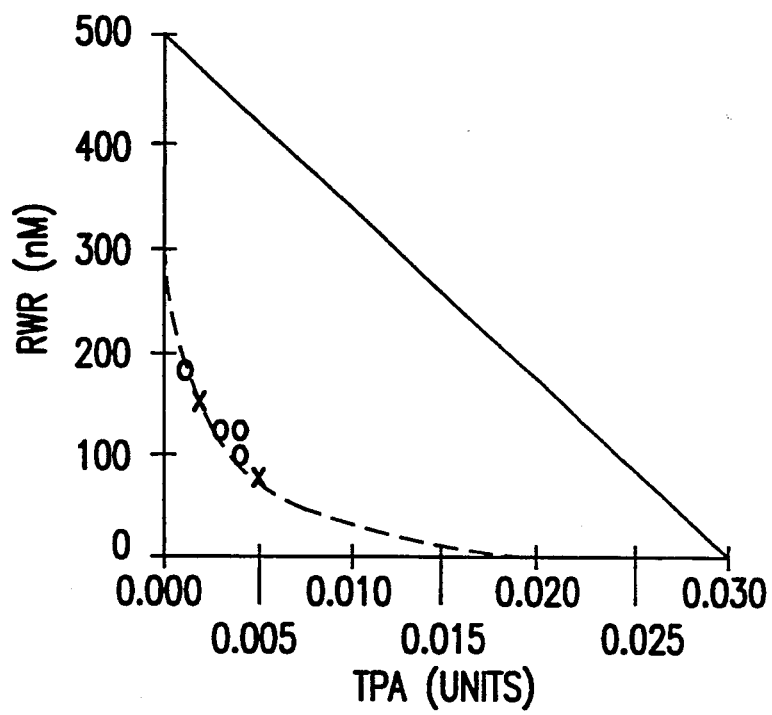
FIG. 11 depicts an isobologram showing the effects of combinations of RWR and t-PA on plasma clot lysis.

In order to determine the effect of combinations of t-PA and RWR on lysis, an isobole was constructed as recommended by previous studies (Loewe, 1957; Berenbaum, 1981). First, isoeffective doses of t-PA and RWR were determined. Radiolabeled plasma clots were incubated at 37° C. with varying amounts of t-PA (0 to 0.03 units) or RWR (0 to 500 nmol). The percentage lysis at 48 hours was determined (FIG. 11). Control clots (without either agent) had 9.36+0.38% lysis during this study. In this experiment, 0.3 U of t-PA and 500 nmol RWR produced an equivalent amount of lysis (35.5+3.1 vs. 34.3+5.1; mean+SEM).

In the same experiment, various empiric, fractional combinations of RWR and t-PA were also tested. Fractional dose combinations of both agents showing equivalent lysis to 500 nmol RWR or 0.03 U of t-PA are plotted (X) on FIG. 11. Dose combinations of RWR and t-PA which produced the same amount of lysis (34.2%, 34.9%) as these agents alone are indicated by X.

Figure 10:
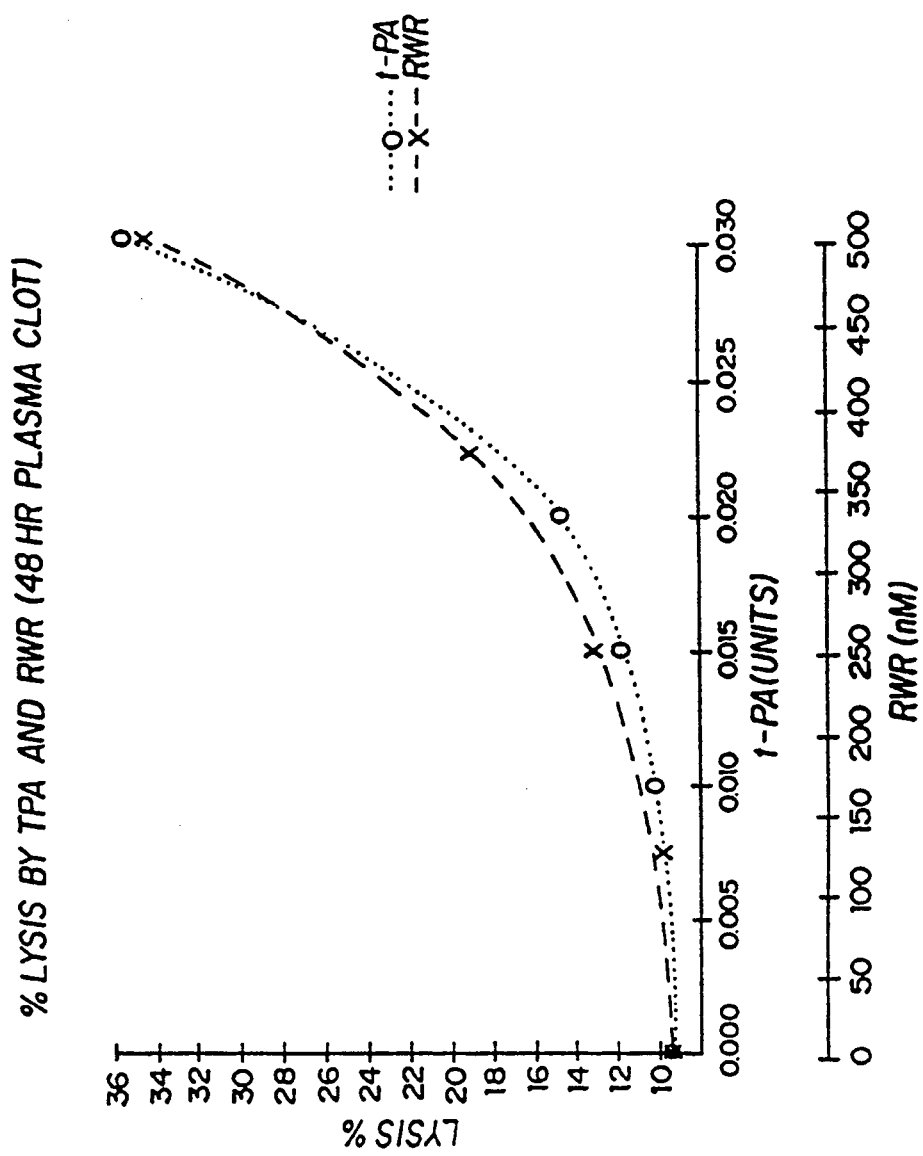
FIG. 10 depicts a graph showing the synergistic effects of t-PA and RWR on plasma clot lysis.

Dose combinations showing higher mean lysis (41.3% to 100%) are denoted by 0. Because the equipotent combinations of t-PA and RWR are a small fraction of each agent alone (i.e., they lie far below the line of additivity indicated by the continuous line in FIG. 10), there is evidence of strong synergy between these two agents.

To avoid mathematical assumptions about the dose-response curves of t-PA and RWR, it was necessary to determine an isoeffective dose for each (i.e., the amount of each agent that produces an equivalent effect). FIG. 7A shows the dose-response curve for t-PA compared with that for RWR. Doses of 0.03 IU/mL of t-PA ($1.2 \times 10^{-3}$ nM) and 500 nM of RWR were found to be isoeffective.

The next step in the analysis was to test the effect on clot lysis of various fractional combinations of RWR and t-PA. The results were then plotted on an isobole, a graph which depicts the isoeffective doses of the two agents alone or in combination. For the purpose of illustration, a hypothetical isobole is shown in FIG. 7'B, inset. If the isoeffective doses of the two agents in combination lie along a straight line drawn between the isoeffective doses of the two agents alone, the agents are additive. If the isoeffective doses lie along a convex line at a greater distance from the origin than from the line of additivity, the agents are antagonistic. But if the two agents in combination lie along a concave line closer to the origin than to the line of additivity, the agents are synergistic.

The empirical isobole for these experiments is shown in FIG. 7B. Filled circles represent the doses of t-PA and RWR alone or in combination that produced equivalent mean lysis (defined as 35±1%). The open circles represent, for the purpose of illustration, the dose combinations of RWR and t-PA that caused even greater mean lysis (41-100%). The fact that such small doses of the two agents in combination produce equal or greater lysis than much larger doses of the two agents alone indicates a potent synergistic interaction between RWR and t-PA.

EXAMPLE 5

A. Plasma Clot Lysis by Plasminogen Activators

One hundred-μL, radiolabeled plasma clots were made as described above. The clots were compressed and washed to remove unbound proteins. To the clot in each tube was added 200 μL fresh-frozen plasma, 75 μL of a plasminogen activator [urokinase (0.31 to 160 IU), t-PA (0.31 to 120 IU), or streptokinase (0.41 to 100 U)]and RWR (1.15 nanomoles) in Tris-buffered saline (pH 7.4) or Tris-buffered saline alone to make a total volume of 325 μL. The tubes were incubated at 37° C. for 1 h. Then 75 μL of ice-cold phosphate buffered saline azide (containing 5,000 kallikrein inhibitor units of aprotinin per mL) was added to each tube to halt plasminolysis. An aliquot of the liquid supernatant was removed and gamma counted, and the percentage of clot lysis was determined. The residual fibrinogen concentration in each tube was immediately assayed in triplicate by the sodium sulfite method (Rampling et al., Clin. Chin Acta 67:43-52 (1976)). To confirm these results fibrinogen levels in the t-PA experiments were also measured by a modified Clauss assay (Vermylen et al., Clin. Chin Acta 8:418-424 (1963)).

The specific activities of the t-PA and urokinase were $4.05 \times 10^{-5}$ nMol per IU and $12.1 \times 10^{-5}$ nMol per IU as measured by an S-2288 assay according to the manufacturer's data sheet. Streptokinase was used as supplied by the manufacturer.

B. Effect of RWR on the Potency of Plasminogen Activators

Figure 12:
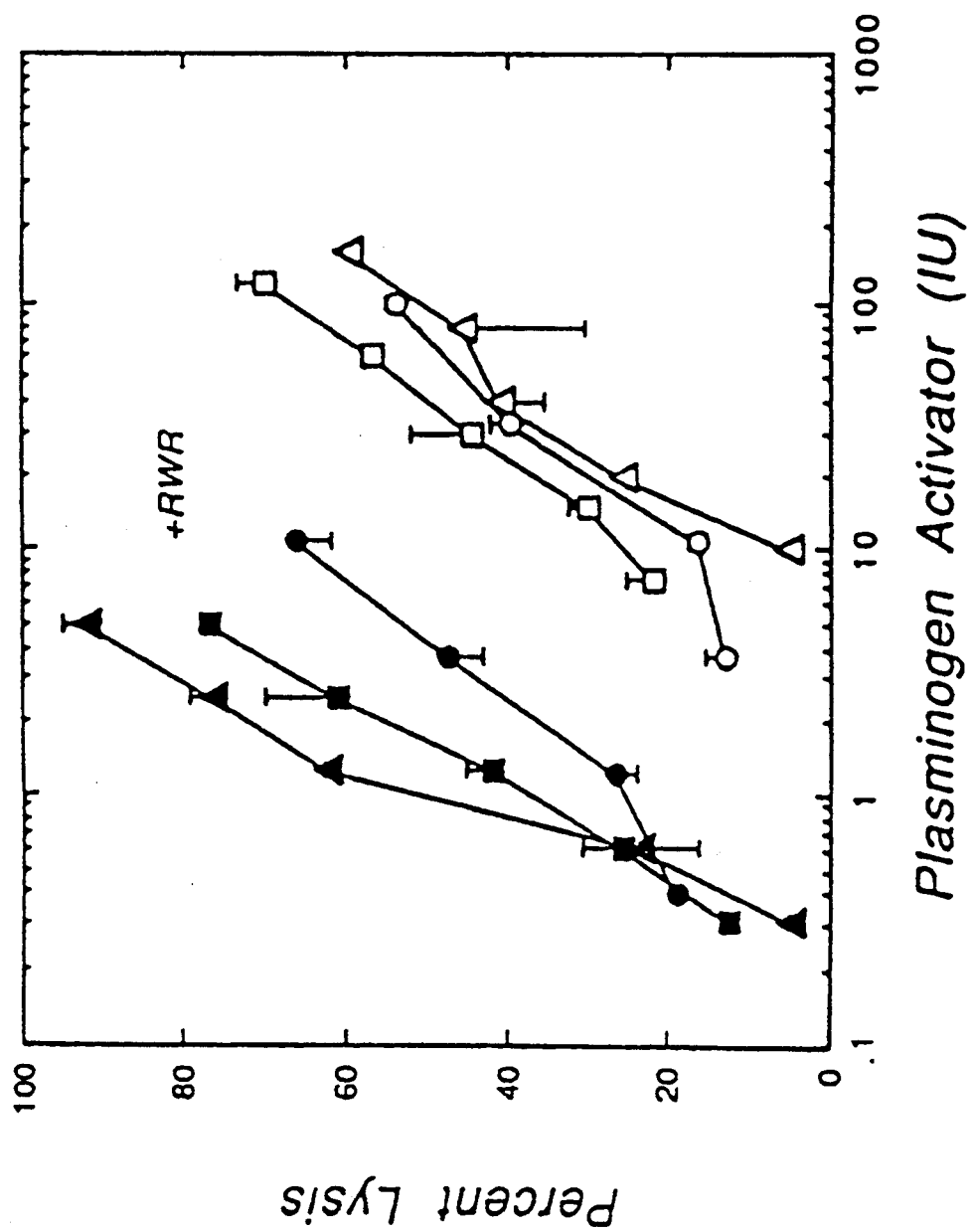
FIG. 12 depicts the effect of monoclonal antibody RWR on the potency of plasminogen activators in a plasma clot lysis assay. Radiolabeled plasma clots were suspended in plasma containing various amounts of urokinase (triangles), t-PA (squares), or streptokinase (circles) with (solid symbols) or without (open symbols) monoclonal antibody RWR. The means±SEM are shown.

The effect of α2AP inhibition on the potency of urokinase, streptokinase, and t-PA was studied in a quantitative clot lysis assay. The results suggest that inhibition of α2AP strikingly increases the potency of all three plasminogen activators. FIG. 12 shows the amount of each activator (log scale) necessary to produce clot lysis in the presence and absence of RWR. A comparison of the amount of urokinase necessary to produce 50% lysis indicates that RWR increases the potency of urokinase by about 80 fold. A similar comparison for t-PA and streptokinase demonstrates that RWR increases the potency of these activators by about 27 fold and 20 fold.

Figure 13C:
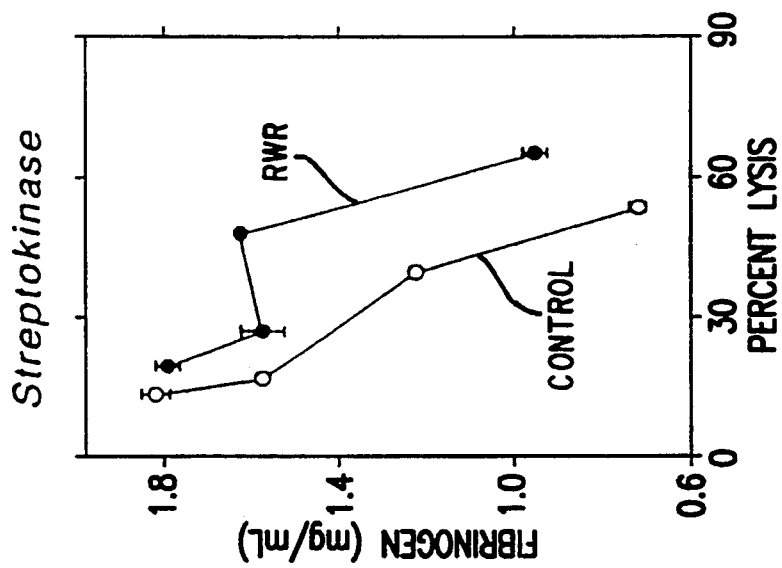
FIG. 13 depicts residual fibrinogen concentrations as a function of plasma clot lysis with and without α2AP inhibition by RWR. The plasma clot lysis experiments were performed as described in FIG. 12, with various amounts of urokinase (triangles in A), t-PA (squares in B) or streptokinase (circles in C) with (solid symbols) or without (open symbols) monoclonal antibody RWR. After 1 hr the residual fibrinogen concentration was measured in triplicate by the sodium sulfite precipitation method (Rampling, M. W. et al., *Clin. Chim. Acta* 67:43–52 (1976)). The means±SEM are shown.
Figure 13B:
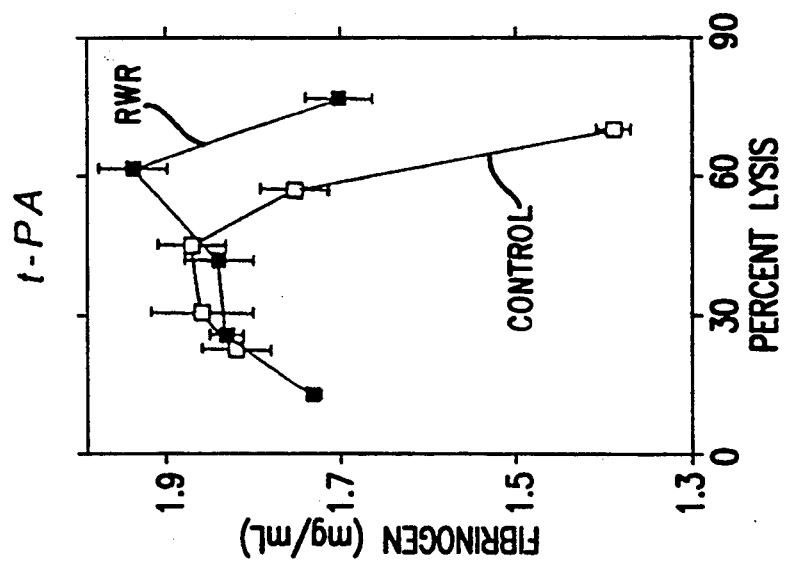
Figure 13A:
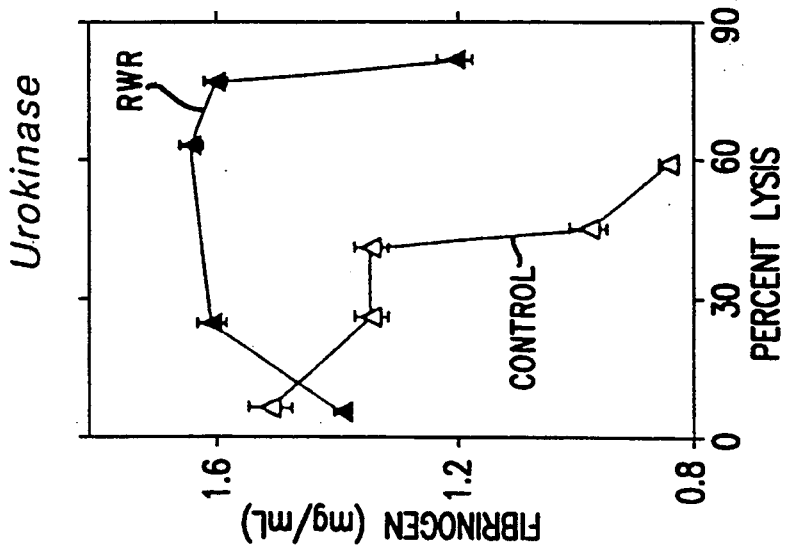

Effect of α2AP Inhibition on the Degradation of Human Fibrinogen. It has been hypothesized that nonspecific proteolysis of clotting factors such as fibrinogen may be associated with a higher risk of bleeding during thrombolytic therapy (Verstraete, M., et. al., Blood 67:1529-1541 (1986)). To study the effect of α2AP inhibition on the specific degradation of fibrin compared with the nonspecific degradation of fibrinogen, we determined the amount of fibrinogen consumption as a function of fibrinolysis. FIG. 13 shows the effects on fibrinogen levels of RWR and the three plasminogen activators (with and without RWR). In clots treated with urokinase alone, fibrinogen levels fell quickly as a function of lysis (FIG. 13A). However, when the clots were treated with urokinase RWR and there was a notable preservation of fibrinogen despite even greater clot lysis. A similar, though less striking, preservation of fibrinogen was seen for t-PA (FIG. 13B) even when, for confirmation, fibrinogen was measured by a different method (Vermylen, C., et al., Clin. Chim. Acta 8:418-424 (1963)) (data not shown). For streptokinase also there was a greater preservation of fibrinogen, as a function of lysis, in the presence of antibody RWR (FIG. 13C).

EXAMPLE 6

Enhancement of in vivo Thrombolysis

A. Materials and Methods

Proteins t-PA with a specific activity of 580,000 IU/mg was purchased from Genentech (South San Francisco, Calif.). MAb RWR and Mab 40-160 (an antidigoxin, control antibody) were raised as described (Reed, G. L., III, et al., Trans. Am. Assoc. 101:250-256 (1988); Mudgett-Hunter, M., et al., Mol. Immunol. 22:477-488 (1985)). Both Mabs were purified from ascites by ammonium sulfate precipitation followed by ion exchange chromatography on DEAE-Affigel Blue (Bio-Rad, Richmond, Calif.). The concentration of Mab RWR was determined by a competition radioimmunoassay similar to that described by Mariani et al. (Mariani, M., et al., J. Immunol. Meth. 92:189-193 (1986)). The concentration of antidigoxin MAb 40-160 was measured by spectrophotometry with an extinction coefficient (1% solution, 1 cm path length) of 1.43. α2AP was purified from human and rabbit plasma by Wiman's method (Wiman, B., Meth. Enzymol. 80:395-408 (1981)).

In Vitro Experiments

Antibody-binding assays were performed to study the binding of Mab to human and rabbit α2AP. Wells of a microtiter plate were coated with 25 μL of a 10 μg/mL solution of human or rabbit α2AP for 1 hour at room temperature. The wells were then rinsed and treated with 100 μL of a 1% solution of bovine serum albumin (RIA grade) in phosphate buffered saline containing 0.02% azide (PBSA) to saturate any nonspecific protein binding sites. The plates were washed again and tapped dry. Dilutions of Mab (from mature hybridoma culture supernatant) were added in triplicate to wells containing human or rabbit α2AP or a control (bovine serum albumin alone). After incubation for 1 hour the wells were washed 8 times and tapped dry. Then 25 μL (about 50,000 cpm) of radioiodinated goat-antimouse(-Fab') antibody (Cappel Laboratories, West Chester, Pa.) was added to each well and allowed to incubate for an hour. Subsequently the unbound radioactive antibody was aspirated, and the plates were washed and dried. The wells were cut out and gamma-counted to determine the amount of bound antibody.

In vitro clot lysis assays were performed with fresh-frozen rabbit plasma collected on citrate and pooled from four normal rabbits. The rabbit plasma was mixed with trace amounts of radioiodinated human fibrinogen (Ibrin; Amersham, Arlington Heights, Ill. Fifty μL of this mixture (about 15,000 cpm) was combined in a test tube with 50 μL of Tris-buffered saline azide (TBSA) containing 30 mM $CaCl_2$. The plasma mixture was then incubated at 37° C. for 1.5 hours to facilitate clotting. The clots were washed with 1 mL of normal saline, which was removed by aspiration. Then 50 μL of Mab RWR (37.5 μg) in TBSA or TBSA alone was added to each tube. The tubes were gamma-counted and 100 μL of TBSA was added to each. The experiment was started by adding 100 μL of t-PA in various amounts (0–10 IU) to the clots. After incubation at 37° C. for 1 hour, 250 μL of ice-cold PBSA containing aprotinin (100 kallikrein inhibitor units/mL) was added to each tube. Immediately thereafter 100 μL of the liquid supernatant was sampled and gamma-counted. The percentage clot lysis was expressed as the ratio of cpm present in the liquid supernatant to cpm remaining in the clot.

Fibrinogen levels were assayed by both the sodium sulfite (Rampling, N. W., *Clin. Chim. Acta* 67:43–52 (1976)) and modified Clauss methods (Vermylen, C., et al., *Clin. Chim. Acta* 8:418–424 (1963)). Residual α2AP activity was measured by a chromogenic (Edy, J., et al., *Thromb. Res.* 8:513–518 (1976)) substrate assay kit from Stachrom (Asnières, France).

In Vivo Thrombolysis Experiments

Thrombolysis was studied in anesthetized rabbits according to the model originally developed by Collen et al., *J. Clin. Invest.* 71:368–376 (1983). The experiments were performed as previously described by our laboratory (Runge, M. S., et al., *Proc. Natl. Acad. Sci. USA* 84:7659–7662 (1987)) with the following modifications. After the $^{125}$I-labeled fibrinogen, human plasma, and red blood cells had clotted in the jugular vein for 30 minutes, t-PA or placebo (saline) was administered by a constant infusion pump through the contralateral, marginal ear vein for 1 hour. In rabbits that received Mab or the control Mab (antidigoxin 40–1607), the antibody was given as a single bolus (1.4 mg/kg, 1–2 mL) immediately before the infusion of t-PA or placebo. Two hours after the t-PA or placebo infusion had been terminated, the jugular vein was ligated, excised, and gamma-counted. The percentage lysis was computed from the ratio of the original vein cpm to the final vein cpm as described (Collen, D., et al., *J. Clin. Invest.* 71:368–376 (1983); Runge, M. S., et al., *Proc. Natl. Acad. Sci. USA* 84:7659–7662 (1987)). Blood samples (1 mL) were collected before the agents were administered and at the end of the study. The samples were collected on sodium citrate (0.38% final) and P-PACK (10.4 μg/mL final) (Sigma, St. Louis, Mo.), centrifuged immediately, and frozen at −80° C. until assay for fibrinogen and α2AP.

All in vivo experiments were performed by one technician who was blinded to the dose of antibody and/or t-PA. Of the 40 thrombolysis experiments completed according to this protocol, 13 were rejected: 8 because of unsatisfactory vein and clot preparation, 4 because of improper infusion of agent, and 1 because of excessive movement due to inadequate sedation. Results from the remaining 27 experiments were analyzed and are reported in detail. At the completion of this series, 2 additional (control) experiments were performed in which the rabbits were given an inert, antidigoxin antibody (Mab 40–160) as a placebo.

The means and SEMs are reported. A two-sample t test was used to compare the means of different groups.

B. Results

Figure 14:
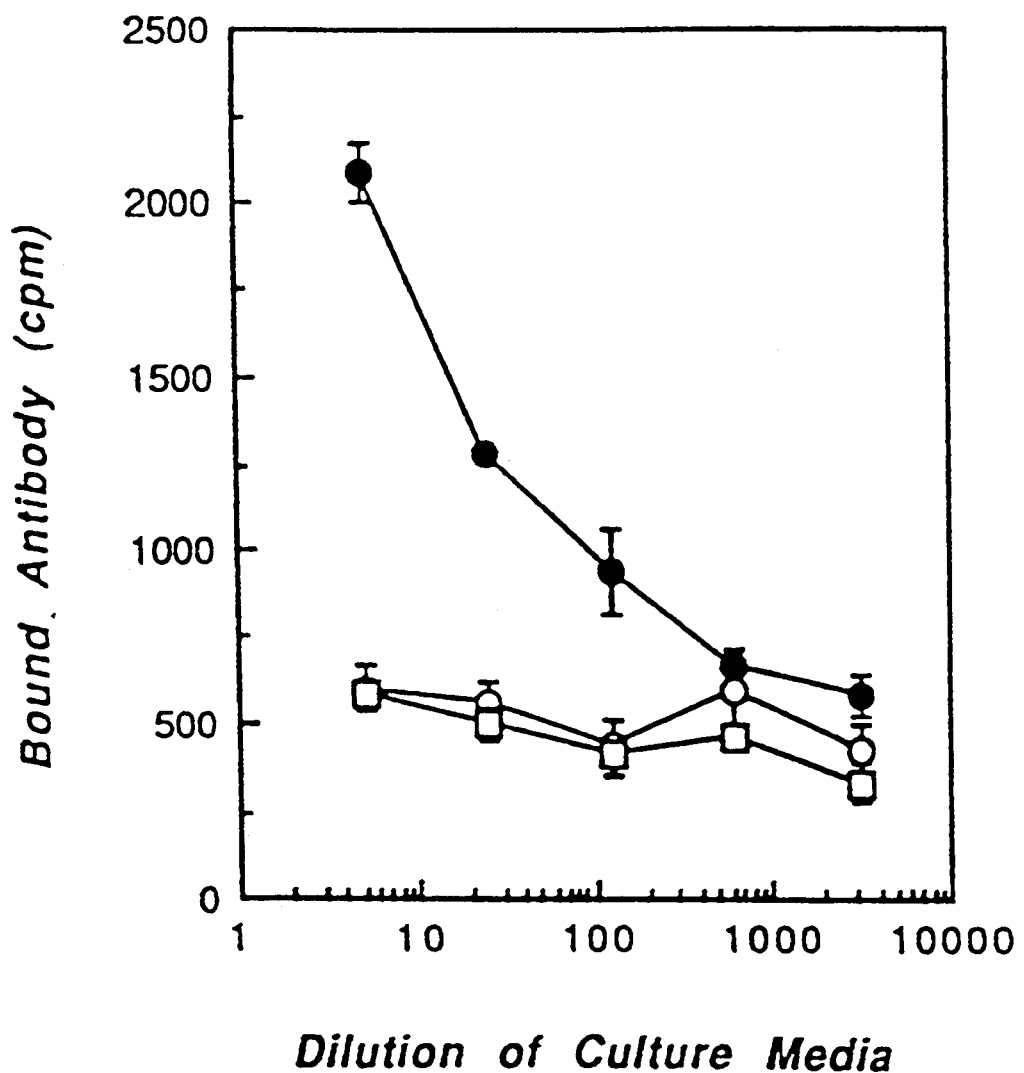
FIG. 14 depicts binding of MAb RWR to human and rabbit α2AP. A solid-phase radioimmunoassay was used to compare the binding of MAb RWR to human α2AP (filled circles), rabbit α2AP (open circles) and control (bovine albumin, squares). Compared with the control MAb, RWR binds significantly to human α2AP but not to the rabbit α2AP. Each point represents the mean (±SEM) of triplicate observations.

Because Mab RWR was selected for its ability to bind to human α2AP, a radioimmunoassay was performed to test its ability to bind to rabbit α2AP. FIG. 14 compares the binding of Mab RWR to human and rabbit α2AP and a control. The data reveal that Mab RWR bound to human α2AP in a concentration-dependent fashion but did not bind significantly to rabbit α2AP.

Figure 15:
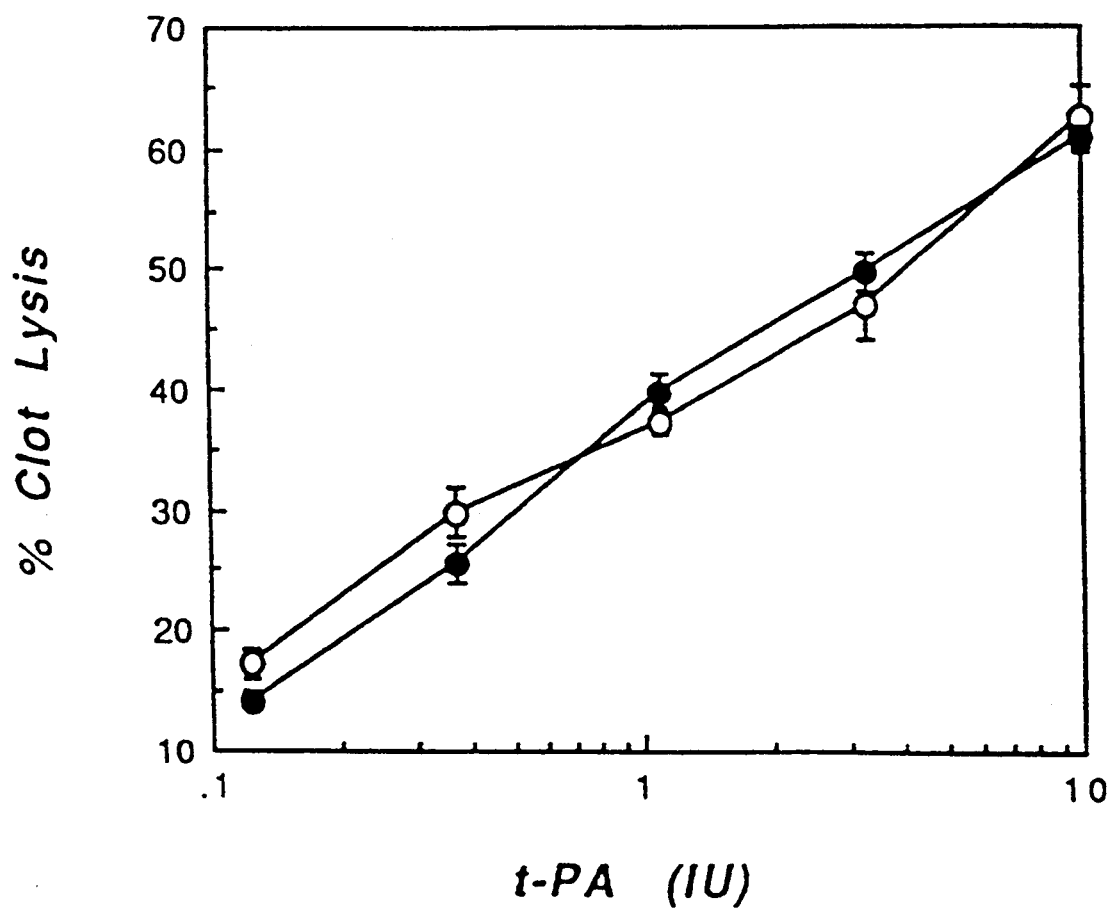
FIG. 15 depicts the effect of MAb RWR on rabbit clot lysis by t-PA in vitro. Pooled, fresh-frozen rabbit plasma was labeled with $^{125}$I-fibrinogen and clotted. Various amounts of t-PA (0.123 to 10 IU) were added to the clots and incubated at 37° C. The percentage clot lysis was compared for clots incubated with MAb RWR (filled circles) and without (open circles). Each point represents the mean±SEM of triplicate observations.

Given that Mab RWR did not appreciably bind to purified rabbit α2AP alone, it was tested whether Mab RWR could bind to and inhibit fibrin-crosslinked or clot-bound rabbit α2AP in an in vitro, rabbit plasma clot lysis assay. In a previous report, it was demonstrated that RWR, because of its ability to bind to and inhibit human α2AP, markedly accelerates the lysis (by 20 to 30 fold) of human plasma clots by t-PA (Reed, G. L., et al., *J Am. Coll. Cardiol.* 13(2):2A (1989)). In a similar assay in rabbit plasma (FIG. 15), though present in molar excess of rabbit α2AP, RWR did not accelerate the lysis of rabbit plasma clots by t-PA. Thus by radioimmunoassay and clot lysis experiments, RWR shows no significant binding or inhibition of rabbit α2AP.

Figure 16:
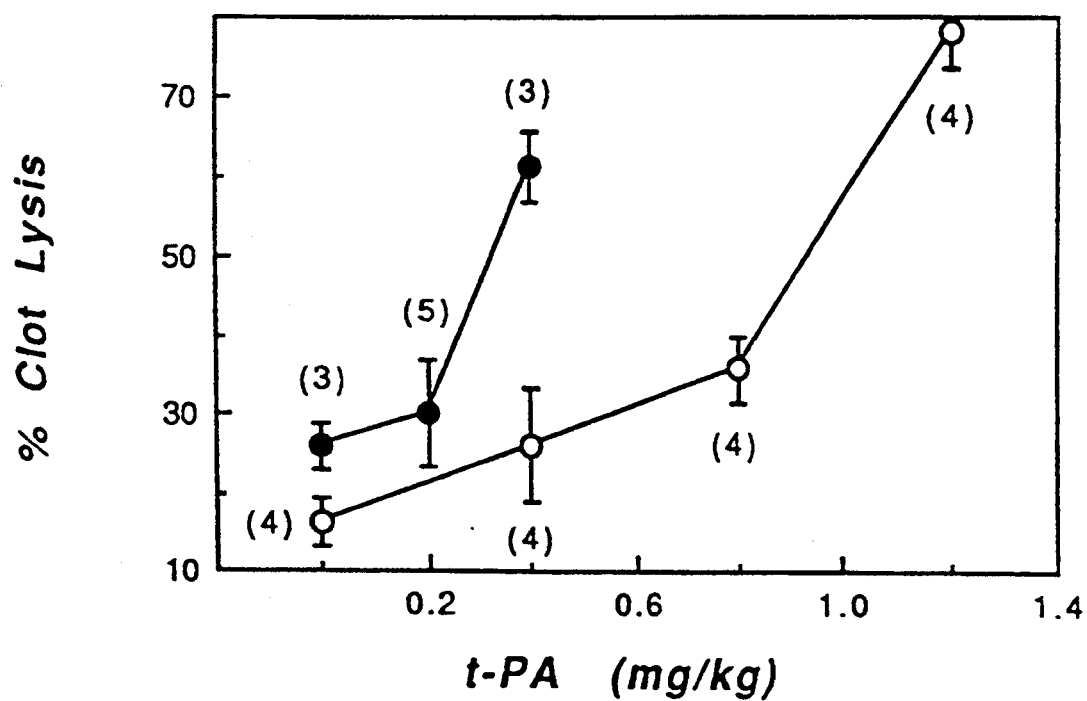
FIG. 16 depicts thrombolysis by t-PA and MAb RWR in vivo. The dose-response curves for t-PA alone (open circles) and for t-PA and MAb RWR in combination (filled circles) are shown. In parentheses is shown the number of rabbits that received each agent. Compared with rabbits receiving equal doses of t-PA alone, the rabbits that received the combination of t-PA and RWR had significantly greater clot lysis (p<0.05). Each point represents the mean lysis±SEM.

Because Mab RWR binds to and inhibits human but not rabbit α2AP, an experimental model was constructed to test the hypothesis that inhibition of clot-bound α2AP would accelerate thrombolysis in vivo. Radiolabeled human clots were formed in rabbit jugular veins to compare the thrombolytic effects of placebo (saline or an inert, control antibody), t-PA, RWR, or the combination of t-PA and RWR. Since Mab RWR only inhibits human α2AP, any thrombolytic effect of the antibody must be due to inhibition of clot-bound (i.e. human) α2AP. FIG. 16 shows the percent clot lysis in rabbits that received t-PA alone or the combination of t-PA and Mab RWR. Rabbits receiving RWR and t-PA showed significantly greater lysis than those receiving an equivalent dose of t-PA alone ($p<0.05$). Compared with the dose-response curve for t-PA alone, the dose-response curve for RWR and t-PA appears shifted to the left and upward, with increasing the thrombolytic potency of t-PA by 2–3 fold.

Figure 17:
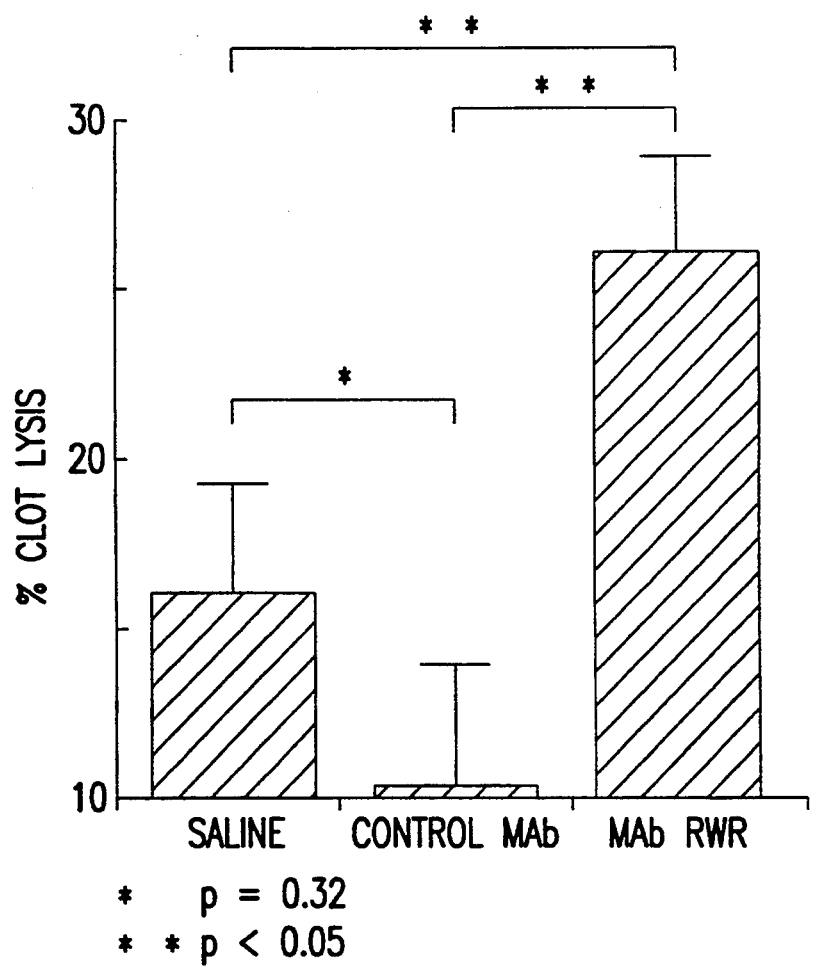
FIG. 17 depicts thrombolysis by MAb RWR in vivo. The amount (mean and SEM) of clot lysis is shown for rabbits receiving saline placebo alone, an inert control of MAb alone, or MAb RWR alone. Compared with saline placebo or the control MAb, MAb RWR caused significantly more clot lysis (p<0.05). There was no significant difference (p=0.32) in the amount of lysis produced by the control MAb compared with the saline placebo.

FIG. 17 compares the amount of lysis in rabbits receiving saline placebo, a control (antidigoxin) antibody, or RWR alone. In rabbits that received saline placebo, mean clot lysis was 16.1±3.1%. In those that received control Mab mean lysis was 10.3±3.8%. However, in rabbits that received RWR without t-PA mean lysis was 25.9±2.8%, which is greater than and significantly different from that obtained in the saline or antibody placebo experiments (p<0.05). Thus in addition to enhancing the thrombolytic potency of exogenous (administered) t-PA, increased thrombolysis by the rabbit's endogenous plasminogen activator.

Figure 18A:
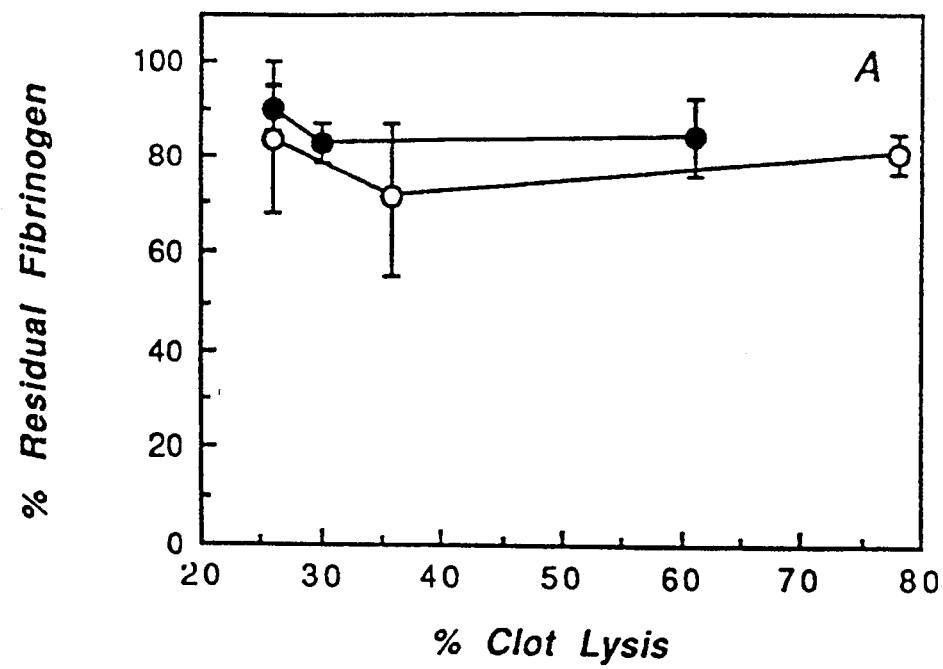
FIG. 18A and B depict fibrinogen consumption by t-PA and MAb RWR. Residual fibrinogen levels were measured by the sulfite precipitation assay (A) or by the modified Clauss assay (B). Each graph shows the mean values±SEM for t-PA alone (open circles) and the combination of MAb RWR and t-PA (filled circles).
Figure 18B:
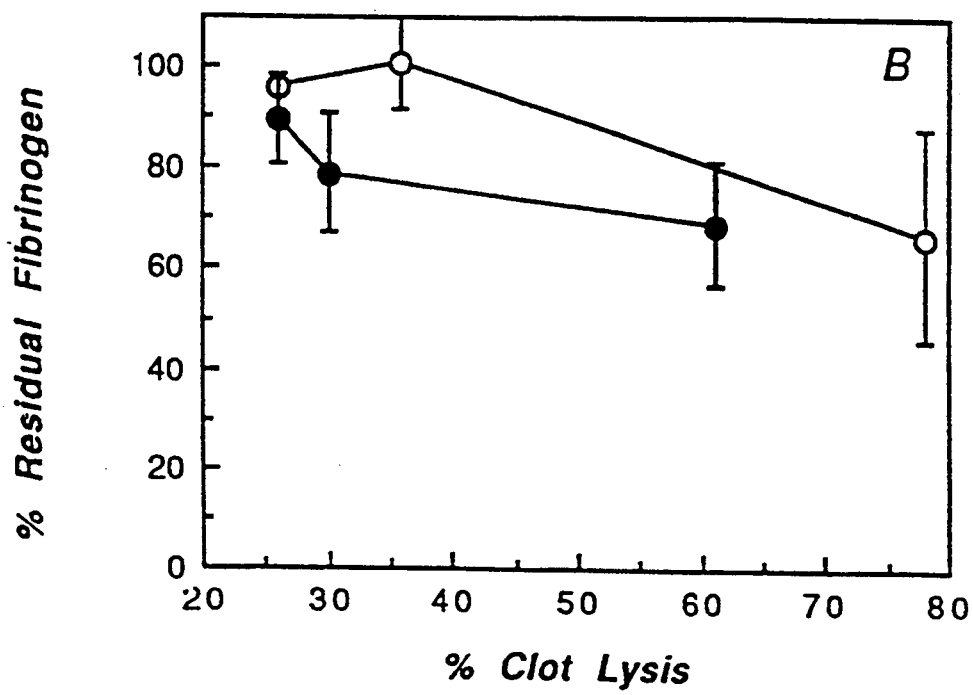
Figure 19:
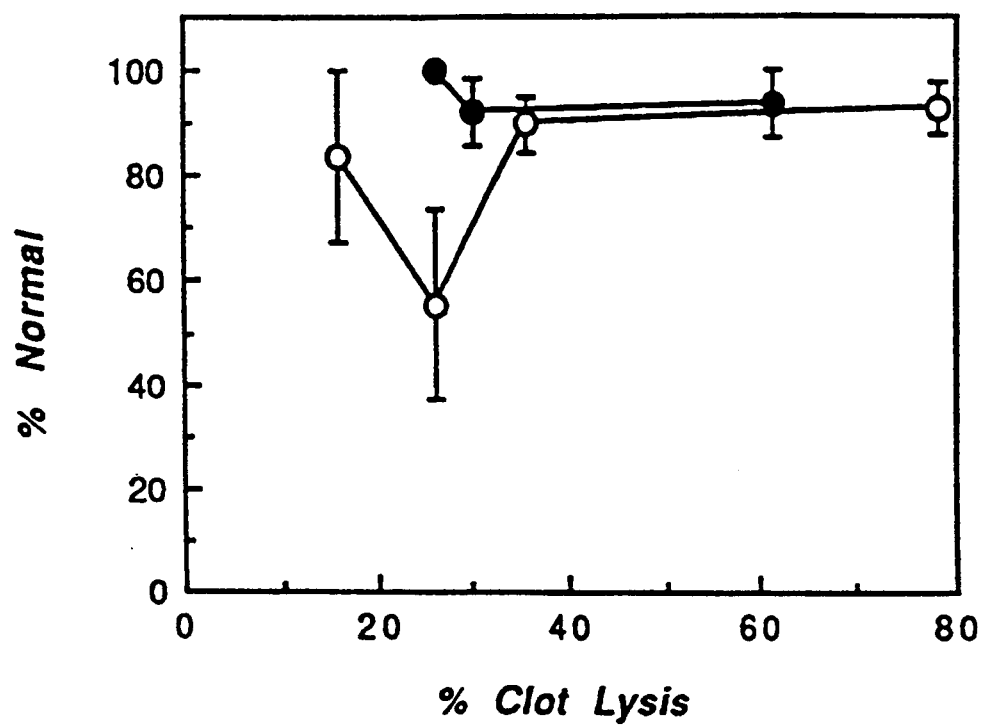
FIG. 19 depicts the effect of t-PA and MAb RWR on rabbit α2AP consumption. The mean residual α2AP levels (±SEM) are shown for rabbits given t-PA alone (open circles) and the combination of t-PA and MAb RWR (filled circles).

To determine whether clot-specific inhibition of α2AP affected the fibrin selectivity of t-PA, RWR the residual fibrinogen levels for RWR and t-PA in combination and those for t-PA alone we measured (FIG. 18, A and B). Fibrinogen levels remained substantially unchanged as a function of clot lysis for both combination and single-agent regimens. Similarly, there was no apparent difference between residual α2AP levels for the two regimens (FIG. 19), confirming our previous results (FIG. 15) that Mab RWR has no measurable inhibitory effect on rabbit α2AP.

EXAMPLE 7

Preferential Binding of Monoclonal Antibody RWR to Fibrin-Bound α-2 Antiplasmin

A. Materials and Methods

Radiolabelled ($^{125}$I) fibrinogen was added to human serum which contains 1 micromolar concentration of antiplasmin. Then thrombin, $CaCl_2$ and Factor 13 were added to crosslink the $^{125}$I fibrin to the antiplasmin. This mixture, which contains approximately 1 micromolar free antiplasmin, and about 1 nanomolar $^{125}$I fibrin-bound antiplasmin, was immunoprecipitated by various antibodies directed against antiplasmin crosslinked to fibrin, or a control, inert (anti-digoxin) antibody. The amount of specifically bound $^{125}$I-fibrin-antiplasmin was determined by gamma scintillation counting and subtracting the background or nonspecific counts as measured by the control antibody.

B. Results and Discussions

Figure 20:
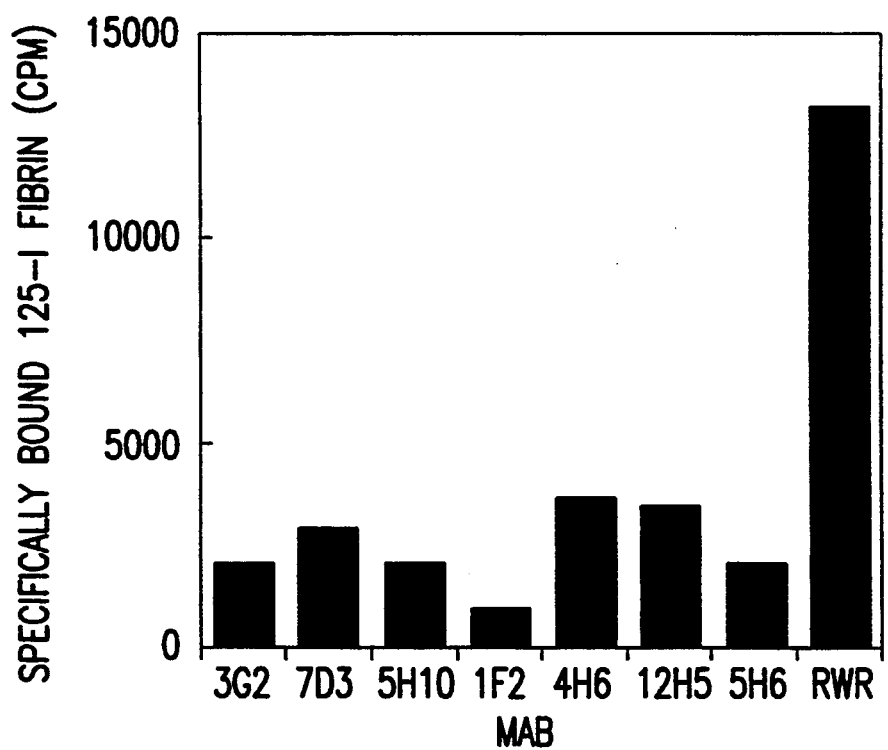
FIG. 20 depicts the capture of $^{125}$I-Fibrin bound α2-antiplasmin in the presence of excess free α-2 antiplasmin.

RWR showed the most binding to the $^{125}$fibrinogen bound antiplasmin compared to the control antibody, or the other antibodies which specifically bind antiplasmin crosslinked to fibrin. See FIG. 20. It should be noted that the concentration of free antiplasmin in the serum is at least a thousand fold greater than that of the anti plasmin crosslinked to fibrin. Thus RWR shows preferential binding to the fibrin crosslinked species of antiplasmin despite a huge excess of the soluble antiplasmin as an inhibitor.

Figure 21:
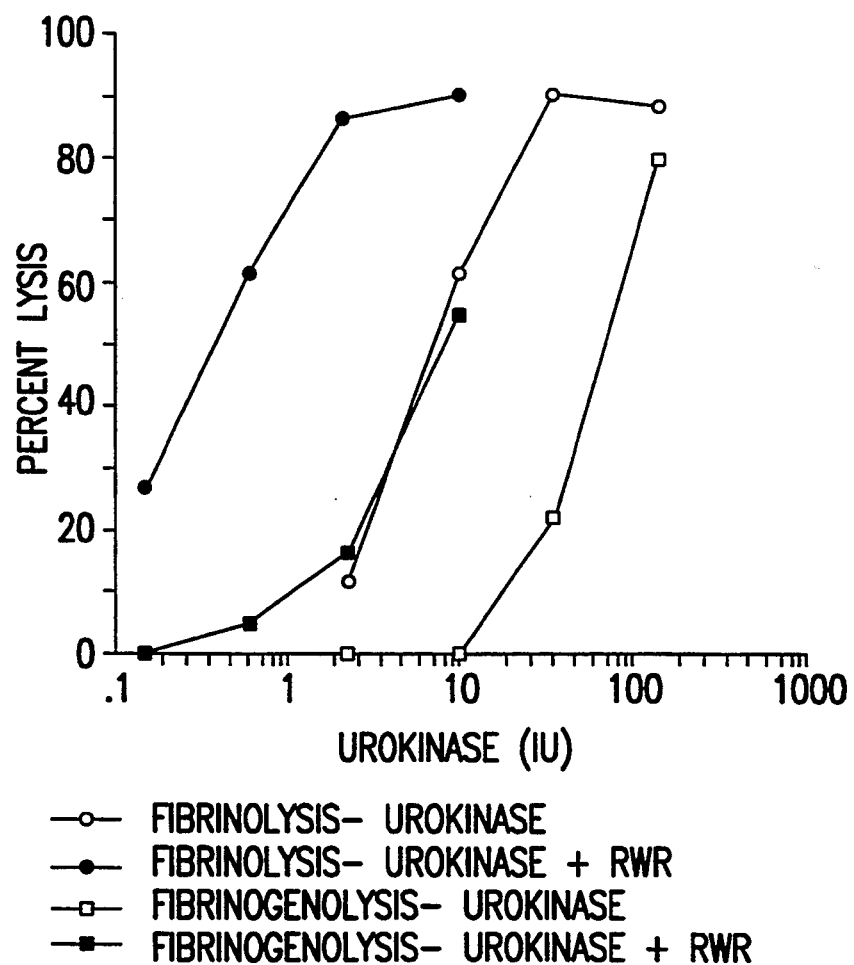
FIG. 21 depicts the relative effects of monoclonal antibody RWR on fibrinogenolysis versus fibrinolysis.

It was further demonstrated that RWR is a more efficient inhibitor of fibrin-bound, or clot-bound, antiplasmin. During the clotting of human plasma approximately 20% of antiplasmin becomes crosslinked to fibrin in the clot. As shown in FIG. 21, we compared the effect of RWR on fibrinogenolysis vs. fibrinolysis by urokinase. RWR or buffer was added to various amounts of urokinase in 100 microliters of normal human plasma or 100 microliters of clotted human plasma. Then dose response curves were constructed that compared the effect of RWR on fibrinolysis (clots) vs. fibrinogenolysis (plasma) by urokinase. Compared to the control clots in this experiment, RWR increased fibrinolysis (in non-clotted plasma) by only 9-fold. Thus the antibody is twice as effective in increasing clot lysis as it is in causing fibrinogenolysis.

This difference in lysis can only arise from the fact that the antibody is a more efficient inhibitor of fibrin-bound (clot-bound) antiplasmin than it is of the soluble antiplasmin in plasma.

It should be noted that fibrin-bound antiplasmin accounts for only 20% of the total antiplasmin in the clotted samples, thus overall, the antibody inhibits clot-bound antiplasmin nearly ten-times better than non-fibrin-bound antiplasmin. A similar preferential inhibition of clot-bound antiplasmin was seen in slightly different experiments using streptokinase and tissue plasminogen activator and was reported in our *Proc. of Natl. Acad. Sci.* paper (1990); 87:FIG. 7-p.1118, and Discussion p.1117, second paragraph).

Having how fully described the invention, it will be appreciated by those skilled in the art that the same can be performed within a wide range of equivalent parameters of composition, conditions, and modes of administration without departing from the spirit or scope of the invention or any embodiment thereof.

What is claimed is:

1. A method of treatment for myocardial infarction or blood clots within a human patient which comprises co-administering to a human patient in need of such treatment:
   a. RWR or a fragment thereof capable of binding human α2-antiplasmin in an amount sufficient to prevent inhibition of plasmin; and
   b. a thrombolytic agent, different from said RWR or fragment thereof, in an amount sufficient to either
      (i) dissolve a fibrin-platelet clot or
      (ii) inhibit the formation of a fibrin-platelet clot, whereby circulating levels of human α2-antiplasmin are not depleted.

2. The method of claim 1, wherein both said RWR or fragment thereof and said thrombolytic agent are provided to said human patient by an intravenous infusion.

3. The method of claim 1, wherein both said RWR or fragment thereof and said thrombolytic agent are provided to said human patient by an intravenously injected bolus.

4. The method of claim 1, wherein said human patient is provided with a first bolus containing said RWR or fragment thereof and a subsequently administered second bolus containing said thrombolytic agent.

5. The method of claim 1, wherein said thrombolytic agent is selected from the group consisting of streptokinase, prourokinase and tissue-type plasminogen activator.

6. The method of claim 5, wherein said thrombolytic agent is tissue-type plasminogen activator.

7. The method of claim 1, wherein:
   (1) said RWR or fragment thereof is provided to said human patient at a dose of between 3 to 6 nmole per kg of patient weight; and
   (2) said thrombolytic agent is provided to said human patient at a dose of between 0.5 to 1.0 mg per kg of patient weight.

8. The method of claim 1, wherein:
   (1) said RWR or fragment thereof is provided to said human patient at a dose of between 3 to 6 nmole per kg of patient weight; and
   (2) said thrombolytic agent is provided to said human patient at a dose of between 0.5 to 0.75 mg per kg of patient weight.

9. A kit useful for carrying out the method of claim 1, being compartmentalized in close confinement to receive two or more container means therein, which comprises:
(1) a first container containing a therapeutically effective amount of said RWR or fragment thereof; and
(2) a second container containing a therapeutically effective amount of said thrombolytic agent.

10. A method of treatment for myocardial infarction or blood clots within a human patient which comprises co-administering to a human patient in need of such treatment:
   a. between 3 to 6 nmole per kg of patient weight of RWR or a fragment thereof capable of binding human $\alpha$2-antiplasmin; and
   b. between 0.5 to 1.0 mg per kg of patient weight of a thrombolytic agent selected from the group consisting of streptokinase, prourokinase, urokinase, and tissue-type plasminogen activator, whereby circulating levels of human $\alpha$2-antiplasmin are not depleted.

11. A method of treatment for myocardial infarction or blood clots within a human patient which comprises co-administering to a human patient in need of such treatment:
   a. between 3 to 6 nmole per kg of patient weight of RWR or a fragment thereof capable of binding human $\alpha$2-antiplasmin; and
   b. between 0.5 to 0.75 mg per kg of patient weight of tissue-type plasminogen activator,
whereby circulating levels of human $\alpha$2-antiplasmin are not depleted.

* * * * *